US006569896B2

(12) United States Patent
Dalton et al.

(10) Patent No.: US 6,569,896 B2
(45) Date of Patent: May 27, 2003

(54) SELECTIVE ANDROGEN RECEPTOR MODULATORS AND METHODS OF USE THEREOF

(75) Inventors: James T. Dalton, Columbus, OH (US); Duane D. Miller, Germantown, TN (US); Donghua Yin, Columbus, OH (US); Yali He, Florence, SC (US)

(73) Assignee: The University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/935,045

(22) Filed: Aug. 23, 2001

(65) Prior Publication Data

US 2002/0099096 A1 Jul. 25, 2002

Related U.S. Application Data

(63) Continuation-in-part of application No. 09/644,970, filed on Aug. 24, 2000.
(60) Provisional application No. 60/300,083, filed on Jun. 25, 2001.

(51) Int. Cl.$^7$ .......................... A01N 32/22; C07C 233/15
(52) U.S. Cl. ....................... 514/493; 514/616; 514/619; 564/153; 564/156; 564/158
(58) Field of Search ................................ 514/493, 616, 514/619; 564/153, 156, 138

(56) References Cited

U.S. PATENT DOCUMENTS

| | | |
|---|---|---|
| 3,875,229 A | 4/1975 | Gold |
| 4,139,638 A | 2/1979 | Neri et al. |
| 4,191,775 A | 3/1980 | Glen |
| 4,239,776 A | 12/1980 | Glen et al. |
| 4,282,218 A | 8/1981 | Glen et al. |
| 4,386,080 A | 5/1983 | Crossley et al. |
| 4,465,507 A | 8/1984 | Konno et al. |
| 4,636,505 A | 1/1987 | Tucker |
| 4,880,839 A | 11/1989 | Tucker |
| 5,162,504 A | 11/1992 | Horoszewicz |
| 5,609,849 A | 3/1997 | Kung |
| 5,656,651 A | 8/1997 | Sovak et al. |
| 6,019,957 A | 2/2000 | Miller et al. |
| 6,071,957 A | 6/2000 | Miller et al. |
| 6,160,011 A | 12/2000 | Miller et al. |
| 2001/0012839 A1 | 8/2001 | Miller et al. |

FOREIGN PATENT DOCUMENTS

| | | |
|---|---|---|
| EP | 0 040 932 | 12/1981 |
| EP | 0 100 172 | 2/1984 |
| WO | WO 95/19770 | 7/1995 |
| WO | WO 98/53826 | 12/1998 |

OTHER PUBLICATIONS

Howard Tucker and Glynne J. Chesterson, J. Med Chem. 1988, 31, pp. 885–887, "Resolution of the Nonsteroidal Antiandrogem—4'–Cyano–3–[4–fluorophenyl)sulfonyl]–2–hydroxy–2–methyl–3'–(trifluoromethyl)–propionanilide and the Determination of the Absolute Configuration of the Active Enantiomer".

D. McKillop, et al., "Enantioselective metabolism and pharmacokinetics of Casodex in the male rat", Xenobiotica, 1995, vol. 25, No. 6, 623–634.

Leonid Kirkovsky, et al., "[$^{125}$I]–Radionated Bicalutamide Analogs as Potential Imaging Agents for Prostate Cancer", Poster Presentation MEDI 155, 214th ACS National Meeting, Las Vegas, NV, Sep. 7–11, 1997, Department of Pharmaceutical Sciences, University of Tennessee, Memphis, TN 38163.

David T. Baird and Anna F. Glasier, "Hormonal Contraception—Drug Therapy", The New England Journal of Medicine, May 27, 1993, pp. 1543–1549.

F.C. W. Wu, "Male Contraception: Current Status and Future Prospects", Clinical Endocrinology, (1988), 29, pp. 443–465.

Carl Djerassi and S.P. Leibo, "A new look at male contraception", Nature, vol. 370, pp. 11–12.

World Health Organisation Task Force on Methods for the Regulation of Male Fertility, "Contraceptive efficacy of testosterone–induced azoospermia in normal men", The Lancet, vol. 336, Oct. 20, 1990, pp. 955–959 and 1517–1518.

C. G. Francisco, et al., "Long–acting contraceptive agents: testosterone esters of unsaturated acids", Steroids, Jan. 1990, vol. 55, Butterworths.

U.S. patent application Ser. No. 09/644,970, Dalton et al., filed Aug. 24, 2000.

U.S. patent application Ser. No. 09/935,044, Dalton et al., filed Aug. 23, 2001.

John M. Hoberman and Charles E. Yesalis, "The History of Synthetic Testosterone", Scientific American, Feb. 1995, pp. 76–81.

Leonid Kirkovsky, et al., "Approaches to Irreversible non–steroidal chiral antiandrogens", Department of Pharmaceutical Sciences, University of Tennessee, 47th Southeast/51st Southwest Joint Regional Meeting of the American Chemical Society, Memphis, TM, Nov. 29–Dec. 1, 1995.

(List continued on next page.)

Primary Examiner—Brian Davis
(74) Attorney, Agent, or Firm—Eitan, Pearl, Latzer & Cohen Zedek, LLP.; Mark S. Cohen

(57) ABSTRACT

This invention provides a novel class of androgen receptor targeting agents (ARTA). The agents define a new subclass of compounds which are tissue-selective androgen receptor modulators (SARM), which are useful for oral testosterone replacement therapy, male contraception, maintaining sexual desire in women, treating prostate cancer and imaging prostate cancer. These agents have an unexpected in-vivo activity for an androgenic and anabolic activity of a nonsteroidal ligand for the androgen receptor. These agents may be active alone or in combination with progestins or estrogens. The invention further provides a novel class of non-steroidal agonist compounds. The invention further provides compositions containing the selective androgen modulator compounds or the non-steroidal agonist compounds and methods of binding an androgen receptor, modulating spermatogenesis, treating and imaging prostate cancer, and providing hormonal therapy for androgen-dependent conditions.

30 Claims, 9 Drawing Sheets

OTHER PUBLICATIONS

David J. Handelsman, "Bridging the gender gap in contraception: another hurdle cleared" The Medical Journal of Australia, vol. 154, Feb. 18, 1996, pp. 230–233.

Edwards JP, Higuchi RI, Winn D T, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano[3,2-g]quinolin-2-one. Bioorg. Med. Chem. Lett., 9: 1003, 1999.

Zhi L, Tegley CM, Marschke KB, and Jones TK. Switching androgen receptor antagonists to agonists by modifying C-ring substituents on piperidino[3,2-g]quinolone. Bioorg. Med. Chem. Lett. 9: 1009, 1999.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl-and 3,4-diaklyl-1,2,3, 4-tetrahydro-8-pyridono[5,6-g]quinolines: potent, nonsteroidal androgen receptor agonists. Bioorg. Med. Chem. Lett., 9:1335, 1999.

Hamann LG, Mani NS, Davis RL, Wang XN, Marschke KB, and Jones TK. Discovery of a potent, orally active nonsteroidal androgen receptor agonist: 4-ethyl-1,2,3, 4-tetrahydro-6-(trifluoromethyl)-8-pyridono[5,6-g]-quinoline (LG121071). J. Med. Chem., 42: 210, 1999.

Rosen J, Day A, Jones TK, Jones ET, Nadzan AM, and Stein RB. Intracellular receptors and signal transducers and activators of transcription superfamilies: novel targets for small- molecule drug discovery. J. Med. Chem., 38: 4855, 1995.

Dalton JT, Mukherjee A, Zhu Z, Kirkovsky L, and Miller DD. Discovery of Nonsteroidal Androgens. Biochem. Biophys. Res. Commun., 244(1):1–4, 1998.

Edwards JP, West SJ, Pooley CLF, Marschke KB, Farmer LJ, and Jones TK. New nonsteroidal androgen receptor modulators based on 4-(trifluoromethyl)-2-(1H)-Pyrololidinol[3,2-g]quinolone. Bioorg. Med. Chem. Lett., 8: 745, 1998.

FIGURE 2. Androgenic and anabolic activity of compound II (S-GTx-007) in rats

FIGURE 3. Androgenic and anabolic activity of compound IV (S-GTx-014) in rats

Fig. 4. Average plasma concentration-time profiles of S-GTx-007 in beagle dogs after IV administration at 3 and 10 mg/kg. Each data point represents the mean ± standard deviation of 3 animals.

FIGURE 5. Average plasma concentration-time profiles of S-GTx-007 in beagle dogs after PO administration as solution at 10 mg/kg. Each data point represents the mean ± standard deviation of 3 animals.

FIGURE 6. Plasma concentration-time profiles of S-GTx-007 in beagle dogs after PO administration as capsules at 10 mg/kg.

GTx-007
Synthetic Outline
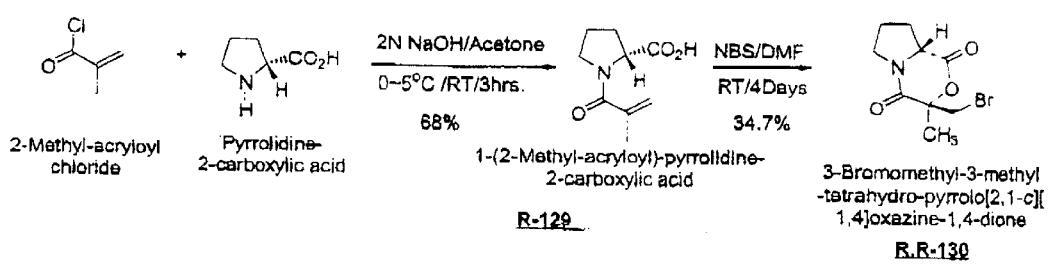
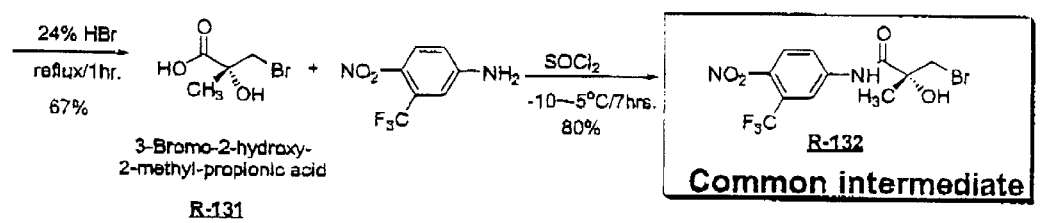
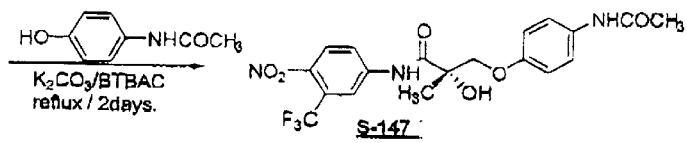
GTx-007
(Acetamidoxolutamide)
Figure 9

SELECTIVE ANDROGEN RECEPTOR MODULATORS AND METHODS OF USE THEREOF

This Application is a Continuation-in-Part Application of U.S. Ser. No. 09/644,970, filed Aug. 24, 2000, converted to provisional 60/367,355 and claims priority of U.S. Ser. No. 60/300,083, filed Jun. 25, 2001, which are hereby incorporated by reference.

GOVERNMENT INTEREST STATEMENT

This invention was made in whole or in part with government support under grant number R29 CA068096 awarded by the National Cancer Institute, National Institute of Health, and under grant number R15 HD35329, awarded by the National Institute of Child Health and Human Development, National Institute of Health. The government may have certain rights in the invention.

FIELD OF INVENTION

The present invention relates to a novel class of tissue-selective androgen receptor targeting agents (ARTA) which demonstrate androgenic and anabolic activity of a nonsteroidal ligand for the androgen receptor. The agents define a new subclass of compounds which are tissue-selective androgen receptor modulators (SARM) which are useful for male hormone therapy such as oral testosterone replacement therapy, mate contraception, maintaining sexual desire in women, treating prostate cancer, and imaging prostate cancer. These agents are also administered to a subject for the treatment of sarcopenia, lack of sexual libido, osteoporosis, erythropoiesis, and fertility. The agents may be used alone or in combination with a progestin or estrogen.

BACKGROUND OF THE INVENTION

The androgen receptor ("AR"") is a ligand-activated transcriptional regulatory protein that mediates induction of male sexual development and function through its activity with endogenous androgens. Androgens are generally known as the male sex hormones. However, androgens also play a pivotal role in female physiology and reproduction. The androgenic hormones are steroids which are produced in the body by the testis and the cortex of the adrenal gland, or synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857–75 (1994). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208–18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone (MENT): The Optimal Androgen For Male Contraception," Ann. Med., 25:199–205 (1993) ("Sundaram")). Because the AR is involved in male sexual development and function, the AR is a likely target for effecting male contraception or other forms of hormone replacement therapy. The AR also regulates female sexual function (i.e., libido), bone formation, and erythropoiesis.

Worldwide population growth and social awareness of family planning have stimulated a great deal of research in contraception. Contraception is a difficult subject under any circumstances. It is fraught with cultural and social stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although health concerns over sexually transmitted diseases have made men more aware of the need to develop safe and responsible sexual habits, women still often bear the brunt of contraceptive choice. Women have a number of choices, from temporary mechanical devices such as sponges and diaphragms to temporary chemical devices such as spermicides. Women also have at their disposal more permanent options, such as physical devices like IUDs and cervical caps as well as more permanent chemical treatments, such as birth control pills and subcutaneous implants. However, to date, the only options available for men include the use of condoms or a vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long term methods that require no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al,. "Effect of Chronic Administration of Testosterone Enanthate on Sperm Production and Plasma Testosterone, Follicle Stimulating Hormones, and Luteinizing Hormone Levels: A Preliminary Evaluation of a Possible Male Contraceptive", Fertility and Sterility 28:1320–28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods Ar Regulation of Male Fertility, "Contraceptive Efficacy of Testosterone-Induced Azoospermia and Oligospermia in Normal Men," Fertilily and Sterility 65:821–29 (1996)).

A variety of testosterone esters have been developed that are more slowly absorbed after intramuscular injection and, thus, result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," Fertility and Sterility 65:626–36 (1996)).

SUMMARY OF THE INVENTION

This invention provides a novel class of tissue-selective androgen receptor targeting agents (ARTA). The agents define a new subclass of compounds which are tissue-selective androgen receptor modulators (SARM), which are useful for oral testosterone replacement therapy, male contraception, maintaining sexual desire in women, osteoporosis, treating prostate cancer and imaging prostate cancer. These agents have an unexpected and tissue-selective in-vivo activity for al androgenic and anabolic activity of a nonsteroidal ligand for the AR. These agents selectively act as partial agonists in some tissues, while acting as full agonists in other tissues, providing a a novel and unexpected means for eliciting tissue-selective androgenic or anabolic effects. These agents may be active alone or in combination with progestins or estrogens. The invention further provides a novel class of non-steroidal agonist compounds. The invention further provides compositions containing the selective androgen modulator compounds or the non-steroidal agonist compounds and methods of binding an AR, modulating spermatogenesis, bone formation and/or resorption, treating and imaging prostate cancer, and providing hormonal therapy for androgen-dependent conditions.

The present invention relates to a selective androgen receptor modulator compound having tissue-selective in-vivo androgenic and anabolic activity of a nonsteroidal ligand for the androgen receptor, the selective androgen receptor modulator compound represented by the structure of formula I:

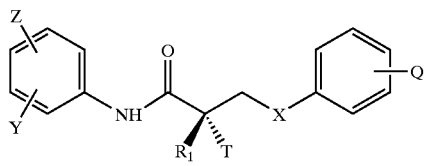

wherein

X is a O, $CH_2$, NH, Se, PR, or NR;

Z is $NO_2$, CN, COR, COOH or CONHR;

Y is I, $CF_3$, Br, Cl, or $SnR_3$;

Q is alkyl, halogen, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR wherein R is a alkyl, aryl, hydroxy, $C_1$–$C_4$ alkyl, a $C_1$–$C_4$ haloalkyl, phenyl, halo, alkenyl or hydroxyl;

or Q together with the benzene ring to which it is attached is a fused ring system represented by structure A, B or C:

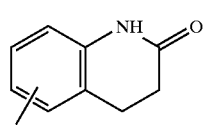

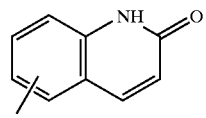

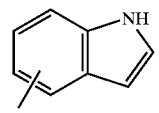

$R_1$ is $CH_3$, $CF_3$, $CH_2CH_3$, or $CF_2CF_3$; and

T is OH, OR, —$NHCOCH_3$, or NHCOR wherein R is a $C_1$–$C_4$ alkyl, a $C_1$–$C_4$ haloalkyl, phenyl, halo, alkenyl or hydroxyl.

In one embodiment, Q is in the para position. In another embodiment, X is O. In another embodiment, Q is in the para position and X is O. In yet another embodiment, Q is para alkyl, halogen, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR wherein R is a alkyl, aryl, hydroxy, $C_1$–$C_4$ alkyl, $C_1$–$C_4$ haloalkyl, phenyl, halo, alkenyl or hydroxyl.

The present invention relates to a selective androgen receptor modulator compound having in-vivo androgenic and anabolic activity of a nonsteroidal ligand for the androgen receptor, the selective androgen receptor modulator compound represented by the structure of formula II:

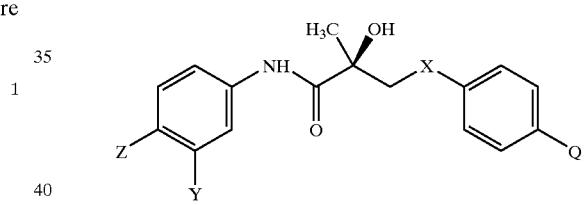

where

X is a O, $CH_2$, NH, Se, PR, or NR;

Z is a hydrogen bond acceptor, $NO_2$, CN, COR, CONHR;

Y is a lipid soluble group, I, $CF_3$, Br, Cl, $SnR_3$;

R is an alkyl or alkyl group or OH; and

Q is acetamido-, trifluroacetamido-, alkylamines, ether, alkyl, N-sulfonyl, O-sulfonyl, alkylsulfonyl, carbonyl, or a ketone.

The present invention also relates to a selective androgen receptor modulator compound having in-vivo androgenic and anabolic activity of a nonsteroidal ligand for the androgen receptor the, selective androgen receptor modulator compound represented by the structure of formula III:

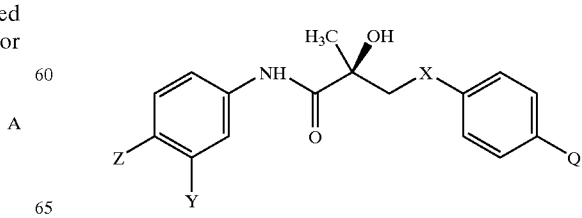

where

X is a O, $CH_2$, NH, Se, PR, or NR;

Z is $NO_2$, CN, COR, CONHR;

Y is a lipid soluble group, I, $CF_3$, Br, Cl, $SnR_3$;

R is an alkyl, or alkyl group or OH; and

Q is acetamido or trifluroacetamido.

The present invention also relates to a selective androgen receptor modulator compound having tissue-selective in-vivo androgenic and anabolic activity of a nonsteroidal ligand for the androgen receptor, the selective androgen receptor modulator compound represented by the structure of formula IV:

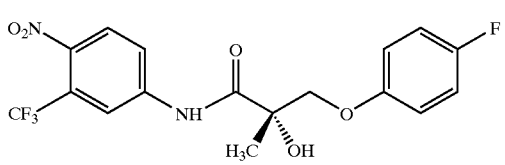

IV

The present invention also relates to a selective androgen receptor modulator compound having tissue-selective in-vivo androgenic and anabolic activity of a nonsteroidal ligand for the androgen receptor, the selective androgen receptor modulator compound represented by the structure of formula V:

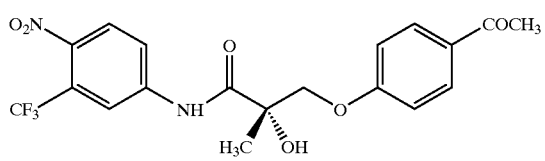

V

The present invention also relates to a selective androgen receptor modulator compound having tissue-selective in-vivo androgenic and anabolic activity of a nonsteroidal ligand for the androgen receptor, the selective androgen receptor modulator compound represented by the structure of formula VI:

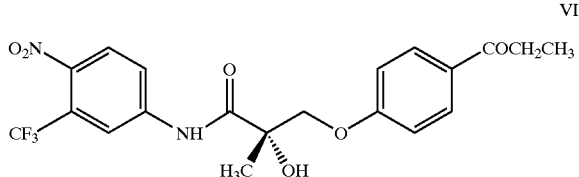

VI

The present invention also relates to a selective androgen receptor modulator compound having tissue-selective in-vivo androgenic and anabolic activity of a nonsteroidal ligand for the androgen receptor, the selective androgen receptor modulator compound represented by the structure of formula VII:

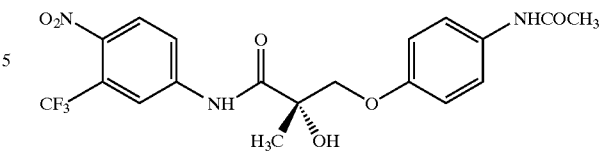

VII

The present invention also relates to a method of binding a selective androgen receptor modulator compound to an androgen receptor, which includes contacting the androgen receptor with the selective androgen receptor modulator compound under conditions effective to bind the selective androgen receptor modulator compound to the androgen receptor. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

Another aspect of the present invention relates to a method of modulating spermatogenesis in a subject, which includes contacting an androgen receptor of the subject with a selective androgen receptor modulator compound under conditions effective to increase or decrease sperm production. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention also relates to a method of hormone therapy, comprising contacting an androgen receptor of a subject with a selective androgen receptor modulator compound under conditions effective to bind the selective androgen receptor modulator compound to the androgen receptor and effect a change in an androgen-dependent condition. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention also relates to a method of treating a subject having a hormone related condition which comprises contacting an androgen receptor of said subject with a selective androgen receptor modulator compound under conditions effective to bind the selective androgen receptor modulator compound to the androgen receptor and effect a change in an androgen-dependent condition. In one embodiment, the selective androgen receptor modulator compound is selective for androgen or testosterone receptor. The present invention also relates to a method of oral administration of the selective androgen receptor modulator compound.

The present invention also relates to a method of treating a subject having prostate cancer which comprises administering to a subject an effective amount of a selective andro gen receptor modulator compound. In one embodiment, the selective androgen receptor modulator compound is selective for androgen or testosterone receptor. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention also relates to compositions and a pharmaceutical compositions which comprises a selective androgen receptor modulator alone or in combination with a progestin or estrogen and a suitable carrier, diluent or salt. In one embodiment the composition comprises Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention relates to a non-steroidal agonist compound, the non-steroidal agonist compound represented by the structure of formula VIII:

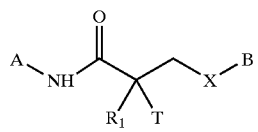

VIII wherein
X is a O, $CH_2$, NH, Se, PR, or NR;
$R_1$ is $CH_3$, $CF_3$, $CH_2CH_3$, or $CF_2CF_3$;
T is OH, OR, —$NHCOCH_3$, or NHCOR wherein R is a $C_1$–$C_4$ alkyl, a $C_1$–$C_4$ haloalkyl, phenyl, halo, alkenyl or hydroxyl;
A is a 5 or 6 membered saturated, unsaturated or aromatic carbocyclic or heterocyclic ring represented by the structure:

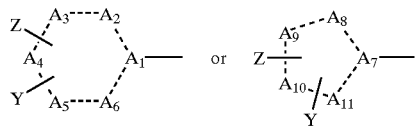

B is a 5 or 6 membered saturated, unsaturated or aromatic carbocyclic or heterocyclic ring represented by the structure:

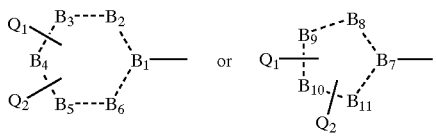

wherein
$A_1$–$A_{11}$ are each C, O, S or N;
$B_1$–$B_{11}$ are each C, O, S or N;
Z is $NO_2$, CN, COOH COR, or CONHR;
Y is I, $CF_3$, Br, Cl, or $SnR_3$; and $Q_1$ and $Q_2$ are independently of each other alkyl, halogen, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR wherein R is a $C_1$–$C_4$ alkyl, a $C_1$–$C_4$ haloalkyl, phenyl, halo, alkenyl or hydroxyl.

The present invention also relates to a composition and pharmaceutical composition comprising the non-steroidal agonist compound alone or in combination with a progestin or estrogen and a suitable carrier, diluent or salt. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention also relates to a method of binding a non-steroidal agonist compound to an androgen receptor comprising contacting the androgen receptor with the non-steroidal agonist compound under conditions effective to bind the non-steroidal agonist compound to the androgen receptor In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention also relates to a method of modulating spermatogenesis in a subject comprising contacting an androgen receptor of the subject with a non-steroidal agonist compound under conditions effective to increase or decrease sperm production. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention also relates to a method of hormone therapy comprising contacting an androgen receptor of a subject with a non-steroidal agonist under conditions effective to bind the non-steroidal agonist compound to the androgen receptor and effect a change in an androgen-dependent condition. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention also relates to a method of treating a subject having a hormone related condition which comprises contacting an androgen receptor of said subject with a non-steroidal agonist compound under conditions effective to bind the non-steroidal agonist compound to the androgen receptor and effect a change in an androgen-dependent condition. In one embodiment, the non-steroidal agonist compound is selective for androgen or testosterone receptor.

The present invention also relates to a method of oral administration of the non-steroidal agonist compound. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention also relates to a method of treating a subject having prostate cancer which comprises administrating to a subject an effective amount of a non-steroidal agonist compound. In one embodiment, the non-steroidal agonist compound is selective for androgen or testosterone receptor. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

Still another aspect of the present relates to a method of producing a selective androgen receptor modulator or a non-steroidal AR agonist compound of the present invention. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The present invention further relates to a method of determining the presence of a selective androgen modulator compound and/or a non-steroidal agonist compound of the present invention in a sample. The method comprises the steps of obtaining the sample, and detecting the compound in the sample, thereby determining the presence of the compound in the sample. In one embodiment, the sample is a blood serum, plasma, urine, or saliva sample. In another embodiment, the detection step comprises measuring the absorbance of the compound. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The novel selective androgen receptor modulator compounds and the non-steroidal agonist compounds of the present invention, either alone or as a composition, are useful in males and females for the treatment of a variety of hormone-related conditions, such as hypogonadism, sarcopenia, erythropoiesis, erectile function, lack of libido, osteoporesis and fertility. Further, the selective androgen receptor modulator compounds and the non-steroidal agonist compounds are useful for oral testosterone replacement therapy, treating prostate cancer, imaging prostate cancer, and maintaining sexual desire in women. The agents may be used alone or in combination with a progestin or estrogen. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

The selective androgen i receptor modulator compounds and the non-steroidal agonist compounds of the present invention offer a significant advance over steroidal androgen treatment because the selective androgen receptor modulator compounds and the non-steroidal agonist compounds of the present invention have been shown in-vivo to have a tissue-selective androgenic and anabolic activity of a nonsteroidal ligand for the androgen receptor. Moreover, the selective androgen receptor modulator compounds and the non-steroidal agonist compounds of the present invention are not accompanied by serious side effects, lability to oxidative metabolism, inconvenient modes of administration, or high costs and still have the advantages of oral bioavailability, lack of cross-reactivity with other steroid receptors, and long biological half-lives. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

BRIEF DESCRIPTION OF THE DRAWINGS

The present invention will be understood and appreciated more fully from the following detailed description taken in conjunction with the appended drawings in which:

FIG. 9: Synthesis scheme of GTx-007.

DETAILED DESCRIPTION OF THE INVENTION

Figure 1:
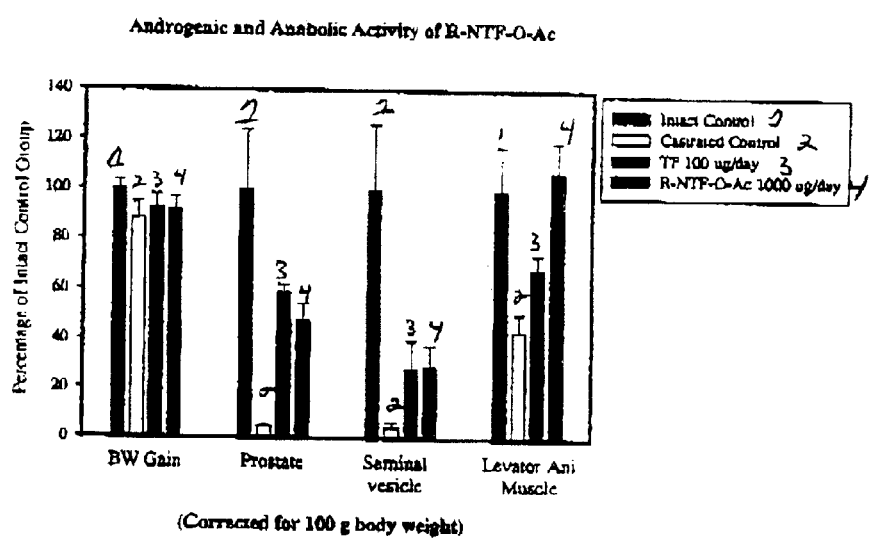
FIG. 1: Androgenic and Anabolic activity of (S)-GTx-007 in rats. Rats were left untreated (intact control), castrated (castrated control), treated with testosterone propionate (TP), or treated with S-GTx-007, and the body weight gain as well as the weight of androgen-responsive tissues (prostate, seminal vesicles and levator ani muscle) was determined.

This invention provides a novel class of androgen receptor targeting agents (ARTA). The agents define a new subclass of compounds which are tissue-selective androgen receptor modulators (SARM) which are useful for oral testosterone replacement therapy, male contraception, maintaining sexual desire in women, treating prostate cancer and imaging prostate cancer. These agents have an unexpected tissue-selective in-vivo activity for an androgenic and anabolic activity of a nonsteroidal ligand for the androgen receptor. These agents may be active alone or in combination with progestinis or estrogens. The invention further provides a novel class of non-steroidal agonist compounds. The invention further provides compositions containing the selective androgen modulator compounds or the non-steroidal agonist compounds and methods of binding an androgen receptor, modulating spermazogenesis, treating and imaging prostate cancer, and providing hormonal therapy for androgen-dependent conditions.

The compounds described herein, define a new class of selective androgen receptor modulators (SARMS) that demonstrate potent anabolic effects (e.g., muscle growth) with less androgenic activity (e.g., prostatic growth). This new class of drugs has several advantages over non-selective androgens, including potential therapeutic applications in males and females for modulation of fertility, erythropoiesis, osteoporosis, sexual libido and in men with or at high risk for prostate cancer. In one embodiment the compound is Compound I. In another embodiment the compound is Compound II. In another embodiment the compound is Compound III. In another embodiment the compound is Compound IV. In another embodiment the compound is Compound V. In another embodiment the compound is Compound VI. In another embodiment the compound is Compound VII. In another embodiment the compound is Compound VIII.

Further, in one embodiment the compounds have tissue specific pharmacologic activity. As demonstarted in FIGS. 7 and 8, GTx-007 does not suppress LH levels at doses that are capable of eliciting maximal stimulation of levator ani muscle growth and does not suppress FSH levels at doses that are capable of eliciting maximal stimulation of levator ani muscle growth.

The present invention relates to a selective androgen receptor modulator compound having tissue-selective in-vivo androgenic and anabolic activity of a nonsteroidal ligand for the androgen receptor selective androgen receptor modulator compound represented by the structure of formula I:

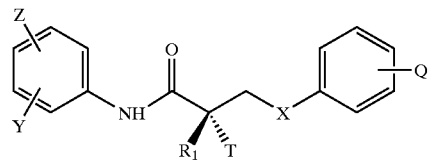

wherein
X is a O, $CH_2$, NH, Se, PR, or NR;
Z is $NO_2$, CN, COR, COOH or CONHR;
Y is I, $CF_3$, Br, Cl, or $SnR_3$;
Q is alkyl, halogen, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR wherein R is an aryl, $C_1$–$C_4$ alkyl, a $C_1$–$C_4$ haloalkyl, phenyl, halo, alkenyl or hydroxyl; or Q together with the benzene ring to which it is attached is a fused ring system represented by structure A, B or C:

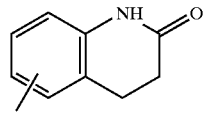

A

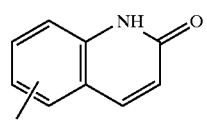

B

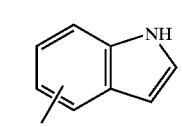

C $R_1$ is $CH_3$, $CF_3$, $CH_2CH_3$, or $CF_2CF_3$; and
T is OH, OR, —$NHCOCH_3$, or NHCOR wherein R is a $C_1$–$C_4$ alkyl, a $C_1$–$C_4$ haloalkyl, phenyl, halo, alkenyl or hydroxyl.

In one embodiment, Q is in the para position of the benzene ring to which it is attached. In another embodiment, Q is in the para position and X is O. In another embodiment, Q is in the para position and is alkyl, halogen, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR wherein R is a, aryl, $C_1$–$C_4$ alkyl, a $C_1$–$C_4$ haloalkyl, phenyl, halo, alkenyl or hydroxyl.

The present invention relates to a selective androgen receptor modulator compound having in-vivo androgenic and anabolic activity of a nonsteroidal ligand for the androgen receptor, the selective androgen receptor modulator compound represented by the structure of formula II:

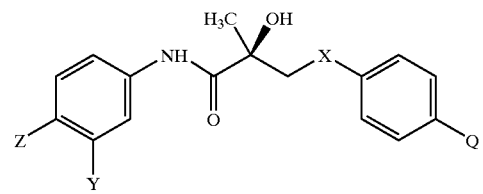

II wherein
X is a O, $CH_2$, NH, Se, PR, or NR;
Z is a hydrogen bond acceptor, $NO_2$, CN, COR, CONHR;
Y is a lipid soluble group, I, $CF_3$, Br, Cl, $SnR_3$;
R is an alkyl or alkyl group or OH; and
Q is acetamido-, trifluroacetamido-, alkylamines, ether, alkyl, N-sulfonyl, O-sulfonyl, alkylsulfonyl, carbonyl, or a ketone.

The present invention also relates to a selective androgen receptor modulator compound having in-vivo androgenic and anabolic activity of a nonsteroidal ligand for the androgen receptor the, selective androgen receptor modulator compound represented by the structure of formula III:

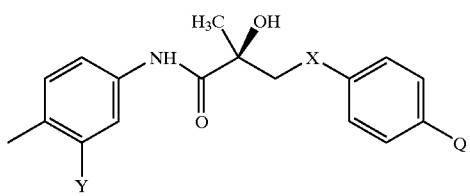

where
X is a O, CH$_2$, NH, Se, PR, or NR;
Z is NO$_2$, CN, COR, or CONHR;
Y is I, CF$_3$, Br, Cl, or SnR$_3$;
R is an alkyl, or aryl group or OH; and
Q is acetamido or trifluroacetamido.

The present invention also relates to a selective androgen receptor modulator compound having tissue-selective in-vivo androgenic and anabolic activity of a nonsteroidal ligand for the androgen receptor, the selective androgen receptor modulator compound represented by the structure of formula IV:

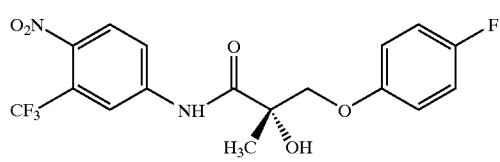

The present invention also relates to a selective androgen receptor modulator compound having tissue-selective in-vivo androgenic and anabolic activity of a nonsteroidal ligand for the androgen receptor, the selective androgen receptor modulator compound represented by the structure of formula V:

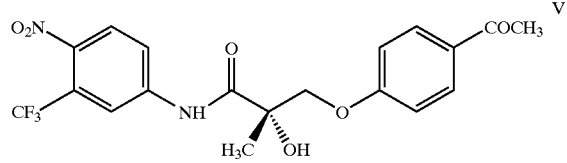

The present invention also relates to a selective androgen receptor modulator compound having tissue-selective in-vivo androgenic and anabolic activity of a nonsteroidal ligand for the androgen receptor, the selective androgen receptor modulator compound represented by the structure of formula VI:

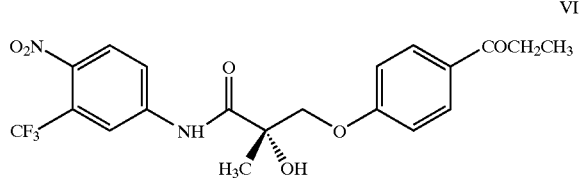

The present invention also relates to a selective androgen receptor modulator compound having tissue-selective in-vivo androgenic and anabolic activity of a nonsteroidal ligand for the androgen receptor, the selective androgen receptor modulator compound represented by the structure of formula VII:

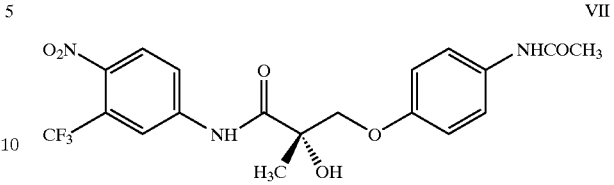

The present invention relates to a non-steroidal agonist compound, the non-steroidal agonist compound represented by the structure of formula VIII:

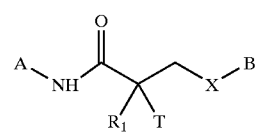

wherein
X is a O, CH$_2$, NH, Se, PR, or NR;
R$_1$ is CH$_3$, CF$_3$, CH$_2$CH$_3$, or CF$_2$CF$_3$;
T is OH, OR, —NHCOCH$_3$, or NHCOR wherein R is a C$_1$–C$_4$ alkyl, a C$_1$–C$_4$ haloalkyl, phenyl, halo, alkenyl or hydroxyl;
A is a 5 or 6 membered saturated, unsaturated or aromatic carbocyclic or heterocyclic ring represented by the structure:

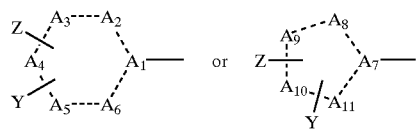

B is a 5 or 6 membered saturated, unsaturated or aromatic carbocyclic or heterocyclic ring represented by the structure:

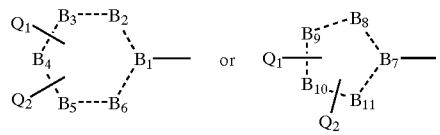

wherein
A$_1$–A$_{11}$ are each C, O, S or N;
B$_1$–B$_{11}$ are each C, O, S or N;
Z is NO$_2$, CN, COOH COR, or CONHR;
Y is I, CF$_3$, Br, Cl, or SnR$_3$; and
Q$_1$ and Q$_2$ are independently of each other alkyl, halogen, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR wherein R is a C$_1$–C$_4$ alkyl, a C$_1$–C$_4$ haloalkyl, phenyl, halo, alkenyl or hydroxyl.

The substitutents Z and Y can be in any position of the five or 6 membered ring carrying these substitutents (hereinafter "A ring"). Similarly, the substituent Q can be in any position of the five or 6 membered ring carrying this substituent (hereinafter "B ring"). It is understood that when any of the ring members $A_1$–$A_{11}$ or $B_1$–$B_{11}$ are O or S, then these ring members are unsubstituted. It is further understood that when any of the ring members $A_1$–$A_{11}$ or $B_1$–$B_{11}$ are O or S, then the dotted line between said ring members and other ring members represents a single bond.

In one embodiment, the A ring includes any type of saturated or unsaturated carbocyclic ring. In one embodiment, the A ring is a 6 membered saturated carbocyclic ring, which may be unsubstituted, monosubstituted or polysubstituted by any of the substitutents described hereinabove. In one embodiment, the A ring is a 5 membered saturated carbocyclic ring, which may be unsubstituted, monosubstituted or polysubstituted by any of the substitutents described hereinabove. In another embodiment, the A ring is a 6 membered carbocyclic ring containing one or more double bonds, which ring may be unsubstituted, monosubstituted or polysubstituted by any of the substitutents described hereinabove. In another embodiment, the A ring is a 5 membered carbocyclic ring containing one or more double bonds, which ring may be unsubstituted, monosubstituted or polysubstituted by any of the substitutents described hereinabove.

In another embodiment, the A ring includes any type of saturated, unsaturated or aromatic heterocyclic ring. In another embodiment, the A ring is a 6 membered saturated heterocyclic ring, which may be unsubstituted, monosubstituted or polysubstituted by any of the substitutents described hereinabove. In another embodiment, the A ring is a 5 membered saturated heterocyclic ring, which may be unsubstituted, monosubstituted or polysubstituted by any of the substituents described hereinabove. In another embodiment, the A ring is a 6 membered heterocyclic ring containing one or more double bonds, which ring may be unsubstituted, monosubstituted or polysubstituted by any of the substitutents described hereinabove. In another embodiment, the A ring is a 5 membered heterocyclic ring containing one or more double bonds, which ring may be unsubstituted, monosubstituted or polysubstituted by any of the substitutents described hereinabove. In another embodiment, the A ring is a 6 membered heteroaromatic ring which may be unsubstituted, monosubstituted or polysubstituted by any of the substitutents described hereinabove. In another embodiment, the A ring is a 5 membered heteroaromatic ring which may be unsubstituted, monosubstituted or polysubstituted by any of the substitutents described hereinabove.

Similarly, the B ring includes any type of saturated or unsaturated carbocyclic ring. In one embodiment, the B ring is a 6 membered saturated carbocyclic ring, which may be unsubstituted, monosubstituted or polysubstituted by any of the substitutents described hereinabove. In one embodiment, the B ring is a 5 membered saturated carbocyclic ring, which may be unsubstituted, monosubstituted or polysubstituted by any of the substitutents described hereinabove. In another embodiment, the B ring is a 6 membered carbocyclic ring containing one or more double bonds, which ring may be unsubstituted, monosubstituted or polysubstituted by any of the substitutents described hereinabove. In another embodiment, the B ring is a 5 membered carbocyclic ring containing one or more double bonds, which ring may be unsubstituted, monosubstituted or polysubstituted by any of the substitutents described hereinabove.

In another embodiment, the B ring includes any type of saturated, unsaturated or aromatic heterocyclic ring. In another embodiment, the B ring is a 6 membered saturated heterocyclic ring, which may be unsubstituted, monosubstituted or polysubstituted by any of the substitutents described hereinabove. In another embodiment, the B ring is a 5 membered saturated heterocyclic ring, which may be unsubstituted, monosubstituted or polysubstituted by any of the substituents described hereinabove. In another embodiment, the B ring is a 6 membered heterocyclic ring containing one or more double bonds, which ring may be unsubstituted, monosubstituted or polysubstituted by any of the substitutents described hereinabove. In another embodiment, the B ring is a 5 membered heterocyclic ring containing one or more double bonds, which ring may be unsubstituted, monosubstituted or polysubstituted by any of the substitutents described hereinabove. In another embodiment, the B ring is a 6 membered heteroaromatic ring which may be unsubstituted, monosubstituted or polysubstituted by any of the substitutents described hereinabove. In another embodiment, the B ring is a 5 membered heteroaromatic ring which may be unsubstituted, monosubstituted or polysubstituted by any of the substitutents described hereinabove.

Nonlimiting examples of suitable A rings and/or B rings are carbocyclic rings such as cyclopentane, cyclopentene, cyclohexane, and cyclohexene rings, and heterocyclic rings such as pyran, dihydropyran, tetrahydropyran, pyrrole, dihydropyrrole, tetrahydropyrrole, pyrazine, dihydropyrazine, tetrahydropyrazine, pyrimidine, dihydropyrimidine, tetrahydropyrimidone, pyrazol, dihydropyrazol, tetrahydropyrazol, piperidine, piperazine, pyridine, dihydropyridine, tetrahydropyridine, morpholine, thiomorpholine, furan, dihydrofuran, tetrahydrofuran, thiophene, dihydrothiophene, tetrahydrothiophene, thiazole, imidazole, isoxazole, and the like.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are Inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across or are transported across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glucocorticoid receptors, and mineralocorticoid, and numerous orphan receptors. The present invention is particularly directed to androgen receptors and all of its isoforms.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration.

The better the ball fits into the socket, the more tightly it is held. This phenomenon is called affinity. If the affinity of a substance is sufficiently high, it will compete with the hormone and bind the binding site more frequently. The binding of the ligand may also lead to tissue-selective recruitment of other important proteins to transduce the signal. These proteins are known as coactivators and corepressor, participate in signal transduction, and may be selectively induced or inhibited by ligand binding. Once bound, signals may be sent through the receptor into the cells, causing tie cell to respond in some fashion. This is called activation. On activation, the activated receptor then directly regulates the transcription of specific genes. But the substance and the receptor may have certain attributes, other than affinity, that activate the cell. Chemical bonds between atoms of the substance and the atoms of the receptors may form. In some cases, this leads to a change in the configuration of the receptor, which is enough to begin the activation process (called signal transduction). As a result, substances can be made which bind receptors and activate them (called receptor agonists) or inactivate them (called receptor antagonists).

The present invention is directed to selective androgen receptor modulator compounds which are agonist compounds, and are, therefore, useful in binding to and activating steroidal hormone receptors. The compounds are non-steroidal. Preferably, the agonist compound of the present invention is an agonist that binds the androgen receptor. Preferably, the compound has high affinity for the androgen receptor. The compound may bind either reversibly or irreversibly to the androgen receptor. The lo compound of the present invention may contain a functional group (affinity label) that allows alkylation of the androgen receptor (i.e. covalent bond formation). Thus, in this case, the compound binds irreversibly to the receptor and, accordingly, cannot be displaced by a steroid, such as the endogenous ligands dihydrotestosterone and testosterone. It is preferable, however, for the compounds of the present invention to reversibly bind the androgen receptor.

According to one aspect of the present invention, a method is provided for binding the selective androgen receptor modulator compounds of the present invention to an androgen receptor by contacting the receptor with a selective androgen receptor modulator compound under conditions effective to cause tie selective androgen receptor modulator compound to bind the androgen receptor. The binding of the selective androgen receptor modulator compounds to the androgen receptor enables the compounds of the present invention to be useful in males and in females in a number of hormone therapies. The agonist compounds bind to and activate the androgen receptor. Binding of the agonist compound is either reversible or irreversible, preferably reversible.

According to one aspect of the present invention, a method is provided for modulating spermatogenesis by contacting an androgen receptor of a patient with a selective androgen receptor modulator compound under conditions effective to bind the selective androgen receptor modulator compound to the androgen receptor and increase or decrease sperm production.

According to another aspect of the present invention, a method is provided for hormonal therapy in a patient (i.e,. suffering from an androgen- dependent condition) which includes contacting an androgen receptor of a patient with a selective androgen receptor modulator compound under conditions effective to bind the selective androgen receptor modulator compound to the androgen receptor and effect a change in an androgen-dependent condition. Androgen-dependent conditions that may be treated according to the present invention include those conditions associated with aging, such as hypogonadism, sacorpenia, erythropoiesis, osteoporosis, and any other conditions later determined to be dependent upon low androgen (e.g., testosterone) levels. In one embodiment, the selective androgen receptor modulator compound is administered alone. In another embodiment, the selective androgen receptor modulator compound is administered in combination with progestin. In yet another embodiment, the selective androgen receptor modulator compound is administered in combination with estrogen.

According to another aspect of the present invention, a method is provided for treating a subject having prostate cancer. The method comprises administrating to a subject an effective amount of a selective androgen receptor modulator compound. In one embodiment, the selective androgen receptor modulator compound is selective for androgen or testosterone receptor.

According to one aspect of the present invention, a method is provided for binding the non-steroidal agonist compounds of the present invention to an androgen receptor by contacting the receptor with a non-steroidal agonist compound under conditions effective to cause the non-steroidal agonist compound to bind the androgen receptor. The binding of the non-steroidal agonist compounds to the androgen receptor enables the compounds of the present invention to be useful in males and in females in a number of hormone therapies. The agonist compounds bind to and activate the androgen receptor. Binding of the agonist compound is either reversible or irreversible, preferably reversible.

According to one aspect of the present invention, a method is provided for modulating spermatogenesis by contacting an androgen receptor of a patient with a non-steroidal agonist compound under conditions effective to bind the selective androgen receptor modulator compound to the androgen receptor and increase or decrease sperm production.

According to another aspect of the present invention, a method is provided for hormonal therapy in a patient (i.e., one suffering from an androgen-dependent condition) which includes contacting an androgen receptor of a patient with a non-steroidal agonist compound under conditions effective to bind the non-steroidal agonist compound to the androgen receptor and effect a change in an androgen-dependent condition. Androgen-dependent conditions that may be treated according to the present invention include those conditions associated with aging, such as hypogonadism, sarcopenia, erythropoiesis, osteoporosis, lack of sexual libido and any other conditions later determined to be dependent upon low androgen (e.g., testosterone) levels. In one embodiment, the non-steroidal agonist compound is administered alone. In another embodiment, the non-steroidal agonist compound is administered in combination with progestin. In yet another embodiment, the non-steroidal agonist compound is administered in combination with estrogen.

According to another aspect of the present invention, a method is provided for treating a subject having prostate cancer. The method comprises administrating to a subject an effective amount of a non-steroidal agonist compound. In one embodiment, the non-steroidal agonist compound is selective for androgen or testosterone receptor.

The compounds of the present invention have an assymetric center and can be the R or S isomer, or a mixture of both. In one embodiment, the compounds racemic mixtures of the R and S enantiomers. In another embodiment, the compounds are substantially pure R enantiomers. In another embodiment, the compounds are substantially pure S enantiomers. "Substantially pure" is defined herein as greater than about 95% preponderance of one isomer. Where the above-described processes for the preparation of the compounds of use in the invention give rise to mixtures of stereoisomers, these isomers may be separated by conventional techniques, such as preparative chromatography. The compounds may be prepared in racemic form, or individual enantiomers may be prepared either by enantiospecific synthesis or by resolution As used herein, "pharmaceutical composition" means therapeutically effective amounts of the SARM or the nonsteroidal agonist compound of the present invention, together with suitable diluents, preservatives, solubilizers, emulsifiers, adjuvant and/or carriers A. "therapeutically effective amount" as used herein refers to that amount which provides a therapeutic effect for a given condition and administration regimen. Such compositions are liquids or Lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also comprehended by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As at result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, is polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115–138 (1984). Preferably, a controlled release device is introduced into a subject in proximity to the site of inappropriate immune activation or a tumor. Other controlled release systems are discussed in the review by Langer (Science 249:1527–1533 (1990).

The pharmaceutical preparation can comprise the selective androgen receptor modulator alone, or can farther include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the selective androgen receptor modulator can be administered to a subject by, for example, subcutaneous implantation of a pellet; in a further embodiment, the pellet provides for controlled release of selective androgen receptor modulator over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tablet-forming processes. For oral administration, the selective androgen receptor modulators or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant like stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the SARM agents or the non-steroidal agonist agents or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as aerosols of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof.

In addition, if desired, the composition can contain minor amounts of auxiliary substances such as wetting or emulsifying agents, pH buffering agents, which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the SARM agents or the non-agonist steroidal compounds or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid).

For use in medicine, the salts of the SARM or the non-steroidal agonist compounds will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts, which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

The present invention farther relates to a method of determining the presence of a selective androgen modulator compound and/or a non-steroidal agonist compound of the present invention in a sample. The method comprises the steps of obtaining the sample, and detecting the compound in the sample, thereby determining the presence of the compound in the sample.

In one embodiment, the sample is a blood serum sample. In another embodiment, the sample is a plasma sample. In another embodiment, the sample is a urine sample. In another embodiment, the sample is a saliva sample. In another embodiment, the sample is any other tissue sample.

In one embodiment, the detection step comprises measuring the absorbance of the compound at a predetermined wavelength. For example, the compounds of the present invention absorb in the ultraviolet region of the spectrum, with an absorbency peak at 270 nm. Thus, in one embodiment of the present invention, the compound is detected by monitoring the UV absorbance of the sample at 270 nm. It should be noted that the present invention is not limited to UV absorption, and that any other spectrometric methods of identification are applicable. For example, compounds can be detected by measuring their infra-red or visible absorbance.

In another embodiment, the present invention further provides a method of determining the concentration of a selective androgen receptor modulator compound and/or a non-steroidal agonist compound of the present invention in a sample. The method comprises the steps of obtaining a sample; determining the level of the compound in the sample, and calculating the concentration of the compound in the sample by comparing the level with a standard sample containing a known concentration of the compound. Calibration curves of known concentrations of the compound in the sample, can be obtained, and the concentration of the compound in the test sample is calculated therefrom. By "level" it is meant the absorption level of the compound at the measured wavelength.

In another embodiment, the compound is detected in the sample by contacting the sample with a binding protein which specifically binds to the compound, and determining the amount of binding protein bound to the compound. The concentration of the compound can be determined by measuring the amount of binding protein bound to the compound, and comparing that amount to a standard sample containing a known concentration of the compound—binding protein complex.

Protein levels can be determined according to standard techniques, as described in Sambrook et al. Briefly, a sample obtained from a subject is contacted with a binding protein which specifically binds to a specific compound of the present invention, and the amount of complex formed between the binding protein and the compound is determined. In one embodiment, the binding protein is an antibody which specifically binds to one or more compounds of the present invention. In another embodiment, the binding protein has a detectable label bound thereto, and the complex between the binding protein-label compound is determined by visualizing the complex As defined herein, "contacting" means that the binding protein is introduced into the sample in a test tube, flask, tissue culture, chip, array, plate, microplate, capillary, or the like, and incubated at a temperature and time sufficient to permit the binding component to bind to a cell or a fraction thereof or plasma/serum or a fraction thereof containing the target. Methods for contacting the samples with the binding proteins, or other specific binding components are known to those skilled in the art and may be selected depending on the type of assay protocol to be run. Incubation methods are also standard and are known to those skilled in the art.

"Visualizing" the complex may be carried out by any means known in the art, including, but not limited to, ELISA, radioimmunoassay, flow cytometry, dot blots, western immunoblotting combined with gel electrophoresis, immunohistochemistry at light and electron pe levels, HPLC and mass spectrometry.

Either monoclonal or polyclonal antibodies (as well as any recombinant antibodies) specific for the selective androgen modulator compounds or the non-steroidal agonist compounds of the present invention can be used in the various immunoassays. The antibodies may be delectably labeled, utilizing conventional labeling techniques well-known to the art. As used herein, the term "label" refers to a molecule, which may he conjugated or otherwise attached (i.e., covalently or non-covalently) to a binding protein as defined herein. Labels are known to those skilled in the art. Thus, the antibodies may be labeled with radioactive isotopes, non-radioactive isotopic labels, fluorescent labels, enzyme labels, chemiluminescent labels, bioluminescent labels, free radical labels, or bacteriophage labels, using techniques known in the art. Examples of radioisotopic labels are .sup.3H, .sup.125 I, sup.131 I, .sup.35 S, sup.14 C, etc. Examples of non-radioactive isotopic labels are .sup.55 Mn, .sup.56 Fe, etc. Examples of fluorescence labels are fluorescent labels which are directly labeled with the preferred fluorescence label, or fluorescent labels which are indirectly labeled with the preferred fluorescence label. In the last case, the preferred fluorescence label is conjugated to a secondary antibody, which is directed against the first antibody, such as an anti species Ig antibody. Typical fluorescent labels include, but are not limited to a fluorescein label, an isothiocyanate label, a rhodamine label, a phycoerythrin label, etc., for example fluorescein isothiocyanate (FITC, International Biological Supplies, Melbourne, Fla.), rhodamine, phycoerythrin (P.E., Coulter Corp., Hialeah, Fla.), phycocyanin, allophycocyanin, phycoerythrin-cyanin dye 5 (PECy5, Coulter), label, a phycocyanin label, an allophycocyanin label, an O-phthaldehyde label, a fluorescamine and Texas Red.

Examples of enzyme labels include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Particularly suitable labels include those, which permit analysis by flow cytometry, e.g., fluorochromes. Other suitable detectable labels include those useful in colorimetric enzyme systems, e.g., horseradish peroxidase (HRP) and alkaline phosphatase (AP). Other proximal enzyme systems are known to those of skill in the art, including hexokinase in conjunction with glucose-6-phosphate dehydrogenase.

Additionally, chemiluminescent compounds may be used as labels. Chemiluminescent labels, such as green fluorescent proteins, blue fluorescent proteins, and variants thereof are known. Also bioluminescence or chemiluminescence can be detected using, respectively, NAD oxidoreductase with luciferase and substrates NADH and FNIN or peroxidase with luminol and substrate peroxide. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin. Once labeled, the antibody may be employed to identify and quantify immunologic counterparts (antibody or antigenic polypeptide) utilizing techniques well-known to the art.

The following examples are presented in order to more fully illustrate the preferred embodiments of the invention. They should in no way be construed, however, as limiting the broad scope of the invention.

EXPERIMENTAL DETAILS SECTION

EXAMPLE 1

Nonsteroidal Ligands with Androgenic and Anabolic Activity

The SARM compounds provided herein were designed, synthesized and evaluated for in-vitro and in-vivo pharmacologic activity. The in-vitro androgen receptor binding affinity and ability to maintain androgen dependent tissue growth in castrated animals was studied Androgenic activity was monitored as the ability of the SARM compounds to maintain and/or stimulate the growth of the prostate and seminal vesicles, as measured by weight. Anabolic activity was monitored as the ability of the SARM compounds to maintain and/or stimulate the growth of the levator ani muscle, as measured by weight.

Synthetic Procedures of Compounds I–VIII (2R)-1-Methacryloylpyrrolidin-2-carboxylic Acid (R-129). D-Proline (R-128, 14.93 g, 0.13 mol) was dissolved in 71 mL of 2 N NaOH and cooled in an ice bath; the resulting alkaline solution was diluted with acetone (71 mL). An acetone solution (71 mL) of metacryloly chloride 127 (13.56 g, 0.13 mol) and 2N NaOH solution (71 mL) were simultaneously added over 40 min to the aqueous solution of D-proline in an ice bath. The pH of the mixture was kept at 10–11° C. during the addition of the metacryloly chloride. After stirring (3 h, room temperatures) .the mixture was evaporated in vacuo at a temperature at 35–45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na$_2$SO$_4$, filtered through Celite, and evaporated in vacuo to give the crude product as a colorless oil. Recrystallization of the oil from ethyl ether and hexanes afforded 16.2 (68%) of the desired compound as colorless crystals: mp 102–103° C. (lit. [214] mp 102.5–103.5° C.); the NMR spectrum of this compound demonstrated the existence of two rotamers of the title compound. $^1$H NMR (300 MHz, DMSO-d$_6$) δ 5.28 (s) and 5.15 (s) for the first rotamer, 5.15 (s) and 5.03 (s) for the second rotamer (totally 2H for both rotamers, vinyl CH$_2$), 4.48–4.44 for the first rotamer, 4.24–4.20 (m) for the second rotamer (totally 1H for both rotamers, CH at the chiral canter), 3.57–3.38 (m, 2H, CH$_2$), 2.27–2.12 (1H, CH), 1.97–1.72 (m, 6H, CH$_2$, CH, Me); $^{13}$C NMR (75 MHz, DMSO-d$_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$+80.8° (c=1, MeOH); Anal. Calcd. for C$_9$H$_{13}$NO$_3$: C, 59.00, H 7.15, N 7.65. Found: C 59.13,H 7.19, N 7.61.

(3R,8aR)-3-Bromomethyl-3-methyl-tetrahydro-pyrrolo [2,1-c][1,4]oxazine-1,4-dione (R, R-130). A solution of NBS (23.5 g, 0.132 mol) in 100 mL of DMF was added dropwise to a stirred solution of compound R-129 (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152–154° C. (lit. [214] mp 107–109° C. for the S-isomer); $^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53–3.24 (m, 4H, CH$_2$), 2.30–2.20 (m, 1H, CH), 2.04–1.72 (m, 3H, CH$_2$ and CH), 1.56 (s, 2H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[\alpha]_D^{26}$+124.5° (c=1.3, chloroform); Anal. Calcd. for C$_9$H$_{12}$BrNO$_3$: C 41.24, H 4.61, N 5.34. Found: C 41.46,H 4.64,N 5.32.

(2R)-3-Bromo2-hydroxy-2-methylpropanoic Acid (R-131). A mixture of bromolactone R-130 (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite, and evaporated in vacuo to dryness. Recrystallization from toluene afforded 10.2 g (86%) of the desired compound as colorless crystals: mp 107–109° C. (lit. [214] mp 109–113° C. for the S-isomer); $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300–2500 (COOH), 1730 (C=O), 1449, 1421, 1380, 1292, 1193, 1085 cm$^{-1}$; $[\alpha]_D^{26}$+10.5° (c=2.6, MeOH); Anal. Calcd. for C$_4$H$_7$BrO$_3$: C 26.25, H 3.86. Found: C 26.28, H 3.75.

N-[4-Nitro-3-(trifluoromethyl)phenyl]-(2R)-3-bromo-2-hydroxy-2-methylpropanamide (R-132). Thionyl chloride (8.6 g, 72 mmol) was added dropwise under argon to a solution of bromoacid R-131 (11.0 g, 60 mmol) in 70 mL of DMA at −5 to −10° C. The resulting mixture was stirred for 2 h under the same conditions. A solution of 4-nitro-3-trifluoromethyl-aniline (12.4 g, 60 mmol) in 80 mL of DMA was added dropwise to the above solution, and the resulting mixture was stirred overnight at room temperature. The solvent was removed on Rotavapor using high vacuum oil pump; the residue was diluted with saturated NaHCO$_3$ solution, and extracted with ethyl ether (100 mL×3). Combined extracts were dried over anhydrous Na$_2$SO$_4$, filtered through Celite, and purified by flash chromatography on silica gel, using methylene chloride as eluent to afford 18.0 g (80%) of the desired compound: mp 98–100° C. (R$_f$=0.2, silica gel, CH$_2$Cl$_2$); $^1$H NMR (300 MHz, DMSO-d$_6$) δ 10.54 (s, 1H, NH), 8.54 (d, J=2.1 Hz, 1H, ArH), 8.34 (dd, J=9.0 Hz, J=2.1 Hz, 1H, ArH), 8.18 (d, J=9.0 Hz, 1H, ArH), 6,37 (s, 1H, OH), 3.82 (d, J=10.4 Hz, 1H, CHH$_a$m,) 3.58 (d, J=10.4 Hz, 1H, CHH$_b$), 1.48 (s, 3H, Me); $^{13}$C NMR (75 MHz, DMSO-d$_6$) δ 173.6 (C=O), 143.0, 127.2, 123.2, 122.6 (q, J=33.0 Hz), 122.0 (q, J=271.5 Hz), 118.3 (q, J=6.0 Hz), 74.4, 41.4, 24.9; IR (KBr) 3344 (OH), 1680 (C=O), 1599, 1548 (C=C, Ar), 1427, 1363, 1161 cm$^{-1}$; MS (ESI): m/z 370.8 (M)$^+$; Anal. Calcd. for C$_{11}$H$_{10}$BrN$_2$O$_4$: C 35.60, H 2.72, N 7.55. Found: C 35.68, H 2.72, N 7.49.

N-[4-nitro-3-trifluoromethyl)phenyl]-(2S)-3-[4-(acetylamino)phenoxy]-2-hydroxy-2-methylpropanamide (S-147). The title compound was prepared from compound R-132 (0.37 g, 1.0 mmol), 4-acetamidophenol (0.23 g, 1.5 mmol) K$_2$CO$_3$ (0.28 g, 2.0 mmol), and 10% of benzyltributylammonium chloride as a phase transfer catalyst in 20 mL of methyl ethyl ketone was heated at reflux overnight under argon. The reaction was followed by TLC, the resulting mixture was filtered through Celite, and concentrated in vacuo to dryness. Purification by flash column chromatography on silica gel (hexanes-ethyl acetate, 3:1) yielded 0.38 g (86%) (R$_f$=0.18 hexanes-ethyl acetate, 3:1) of the desired compound as a light yellow powder: mp 70–74° C.; The solid can be recrystalized from ethyl acetate and hexane); $^1$H NMR (300 MHz, DMSO-d$_6$) δ 10.62 (s, 1H, NH), 9.75 (s, 1H, NH), 8.56 (d, J=1.9 Hz, 1H, ArH), 8.36 (dd, J=9.1 Hz, J=1.9 Hz, 1H, ArH), 8.18 (d, J=9.1 Hz, 1H, ArH), 7.45–7.42 (m, 2H, ArH), 6.85–6.82 (m, 2H, ArH), 6.25 (s, 1H, OH), 4.17 (d, J=9.5 Hz, 1H, CHH$_a$), 3.94 (d, J=9.5 Hz, 1H, CHH$_b$), 1.98 (s, 3H, Me), 1.43 (s, 3H, Me); $^{13}$C NMR (75 MHz, DMSO-d$_6$) δ 174.6 (C=O), 167.7, 154.2, 143.3, 141.6, 132.8, 127.4, 123.0, 122.7 (q, J=33.0 Hz), 122.1 (q, J=271.5 Hz), 120.1, 118.3 (q, J=6.0 Hz), 114.6, 74.9, 73.8, 23.8, 23.0; IR (KBr) 3364 (OH), 1668 (C=O), 1599, 1512 (C=C, Ar), 1457, 1415, 1351, 1323, 1239, 1150 1046 cm$^{-1}$; MS (ESI): m/z 464.1 (M+Na)$^+$; Anal. Calcd. for C$_{19}$H$_{18}$F$_3$N$_3$O$_6$: C 51.71, H 4.11, N 9.52. Found: C 52.33, H 4.40, N 9.01.

The synthesis of the various ether analogs of GTx 007 utilizes the common intermediate that is the final reaction step. Bromo-intermediates are used which allow various phenolic compounds to displace the bromide to give the desired ether product Bromohydrin was converted to an epoxide and to open the epoxide to give the same desired ether product.

The in-vitro activity of the SARM compounds, specifically compound VII, demonstrated high androgen receptor binding affinity (Ki=7.5 nM). Animal studies with the SARM compounds, specifically compound V, demonstrated that it is a potent androgenic and anabolic nonsteroidal agent. Four groups of rats were used for these studies: (1) intact controls, (2) castrated controls, (3) castrated animals treated with testosterone propionate (100 μg/day), and (4) castrated animals treated with compound V (1000 μg/day). Testosterone and compound VII were delivered at a constant rate for 14 days via subcutaneous osmotic pumps.

The results of these studies are shown in FIG. 1. Castration significantly reduced the weight of androgenic (e.g., prostate and seminal vesicles) and anabolic (e.g., levator ani muscle) tissues, but had little effect on animal body weight (BW). Treatment of castrated animals with testosterone propionate or compound VII maintained the weight of androgenic tissues to the same degree. Compound VII had similar androgenic activity as testosterone propionate (i.e., the prostate and seminal vesicle weights were the same), but much greater efficacy as an anabolic agent. Compound VII showed greater anabolic activity than testosterone propionate at the doses tested (i.e., the levator ani muscle maintained the same weight as intact control animals and was greater than that observed for testosterone). The experiments presented herein are the first in-vivo results which demonstrate tissue-selective androgenic and anabolic activity (i.e., differing androgenic and anabolic potency) of a nonsteroidal ligand for the androgen receptor.

EXAMPLE 2

Nonsteroidal Ligands with Androgenic and Anabolic Activity

The in-vivo efficacy and acute toxicity of four novel nonsteroidal androgens (compounds IV, V, VI and VII) in rats was examined. In-vitro assays established that these compounds bind the androgen receptor with very high affinity. The structures and names of the four compounds are presented below:

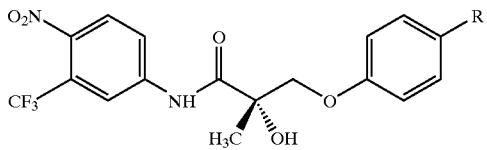

GTx-014 R=F
GTx-015 R=COCH$_3$
GTx-016 R=COC$_2$H$_5$
GTx-007 R=NHCOCH$_3$

EXPERIMENTAL METHODS

Materials. The S-isomers of compounds GTx-014 (compound IV), GTx-015 (compound V), GTx-016 (compound VI) and GTx-007 (compound VII wherein R is NHCOCH3) and the R-isomer of GTx-014 were synthesized in accordance with the scheme as set forth in FIG. 9. Testosterone propionate (TP), polyethylene glycol 300 (PEG300, reagent grade) and neutral buffered formalin (10% w/v) were purchased from Sigma Chemical Company (St Louis, Mo.). Alzet osmotic pumps (model 2002) were purchased from Alza Corp. (Palo Alto, Calif.).

Animals. Immature male Sprague-Dawley rats, weighing 90 to 100 g, were purchased from Harlan Biosciences (Indianapolis, Ind.). The animals were maintained on a 12-hour light-dark cycle with food and water available ad libitum. The animal protocol was reviewed and approved by the Institutional Laboratory Animal Care and Use Committee.

Study Design. Rats were randomly distributed into twenty-nine (29) groups, with 5 animals per group. Treatment groups are described in Table 1. One day prior to the start of drug treatment, animals in groups 2 through 29 were individually removed from the cage, weighed and anesthetized with an intraperitoneal dose of ketamine/xylazine (87/13 mg/kg; approximately 1 mL per kg). When appropriately anesthetized (i.e., no response to toe pinch), the animals' ears were marked for identification purposes. Animals were then placed on a sterile pad and their abdomen and scrotum washed with betadine and 70% alcohol. The testes were removed via a midline scrotal incision, with sterile suture being used to ligate supra-testicular tissue prior to surgical removal of each testis. The surgical wound site was closed with sterile stainless steel wound clips, and the site cleaned with betadine. The animals were allowed to recover on a sterile pad (until able to stand) and then returned to their cage.

Twenty-four hours later, animals in groups 2 through 29 were re-anesthetized with ketamine/xylazine, and an Alzet osmotic pump(s) (model 2002) was placed subcutaneouly in the scapular region. In this instance, the scapular region was shaved and cleaned (betadine and alcohol) and a small incision (1 cm) made using a sterile scalpel. The osmotic pump was inserted and the wound closed with a sterile stainless steel wound clip. Animals were allowed to recover and were returned to their cage. Osmotic pumps contained the appropriate treatment (designated in Table 1) dissolved in polyethylene glycol 300 (PEG300). Osmotic pumps were filled with the appropriate solution one day prior to implantation. Animals were monitored daily for signs of acute toxicity to drug treatment (e.g., lethargy, rough coat).

After 14 days of drug treatment, rats were anesthetized with ketamine/xylazine. Animals were then sacrificed by exsanguinations under anesthesia. A blood sample was collected by venipuncture of the abdominal aorta, and submitted for complete blood cell analysis. A portion of the blood was placed in a separate tube, centrifuged at 12,000 g for 1 minute, and the plasma layer removed and frozen at $-20°C$. The ventral prostates, seminal vesicles, levator ani muscle, liver, kidneys, spleen, lungs, and heart were removed, cleared of extraneous tissue, weighed, and placed in vials containing 10% neutral buffered formalin. Preserved tissues were sent to GTx, Inc. for histopathological analysis.

For data analysis, the weights of all organs were normalized to body weight, and analyzed for any statistical significant difference by single-factor ANOVA. The weights of prostate and seminal vesicle were used as indexes for evaluation of androgenic activity, and the levator ani muscle weight was used to evaluate the anabolic activity.

Results

The androgenic and anabolic activities the S isomers of compounds GTx-014, GTx-015, GTx-016 and GTx-007, and the R isomer of GTx-014 were examined in a castrated rat model after 14 days of administration. Testosterone propionate, at increasing doses, was used as the positive control of anabolic and androgenic effects.

Figure 2:
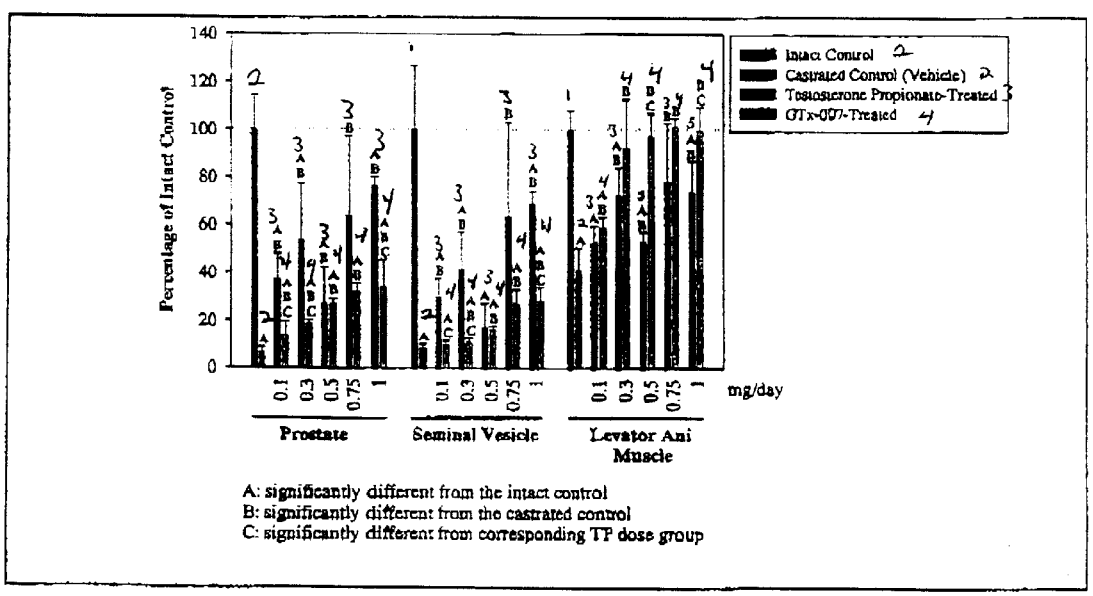
FIG. 2: Androgenic and Anabolic activity of S-GTx-007 in rats. Rats were left untreated (intact control), castrated (castrated control), treated with 0.1, 0.3, 0.5, 0.75 and 1.0 mg/day testosterone propionate (TP), or treated with 0.1, 0.3, 0.5, 0.75 and 1.0 mg/day S-GTx-007, and the weight of androgen-responsive tissues (prostate, semimal vesicles and levator ani muscle) was determined.
Figure 3:
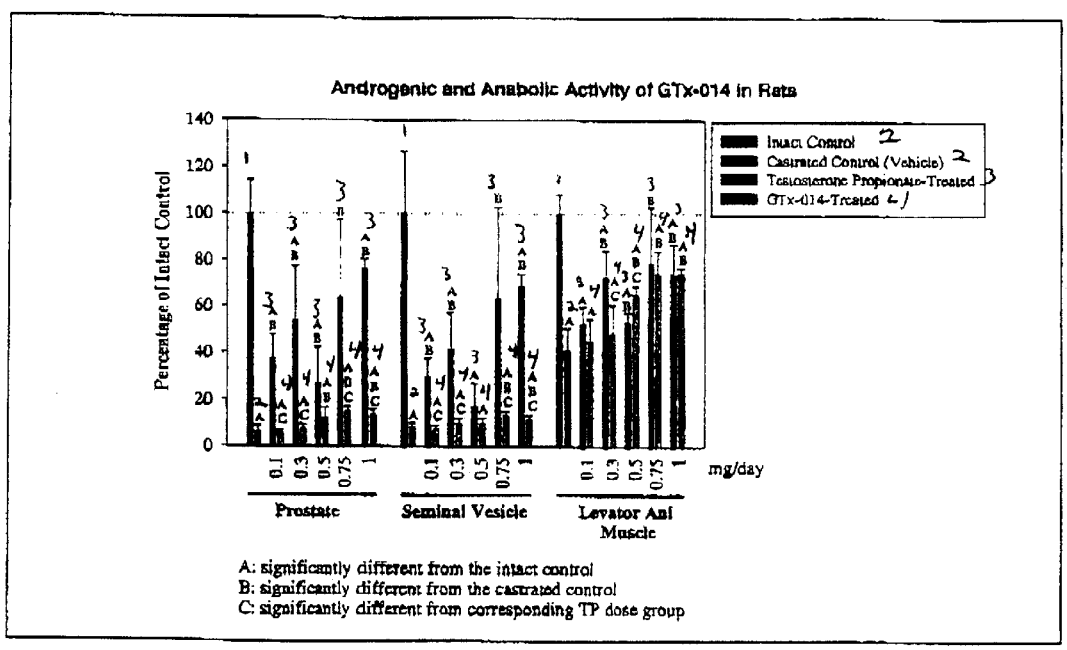
FIG. 3: Androgenic and Anabolic activity of S-GTx-014 in rats. Rats were left untreated (intact control), castrated (castrated control), treated with 0.1, 0.3, 0.5, 0.75 and 1.0 mg/day testosterone propionate (TP), or treated with 0.1, 0.3, 0.5, 0.75 an d 1.0 mg/day S-GTx-014, and the weight of androgen-responsive tissues (prostate, semimal vesicles and levator ani muscle) was determined.

As shown in FIGS. 2 and 3, the weights of prostate, seminal vesicle, and levator ani muscle in castrated, vehicle-treated rats decreased significantly, due to the ablation of endogenous androgen production. Exogenous administration of testosterone propionate, an androgenic and anabolic steroid, increased the weights of prostate, seminal vesicle, and levator and muscle in castrated rats in a dose-dependent manner The R-isomer of GTx-014, and S-isomers of GTx-015 and GTx-016 showed no effect on the weights of prostate, seminal vesicle, and levator ani muscle in castrated animals (data not shown). The S-isomers of GTx-007 (FIG. 2: S-GTx-007) and GTx-014 (FIG. 3: S-GTx-014) resulted in dose-dependent increases in prostate, seminal vesicle and levator ani muscle weights. Compared with testosterone propionate, S-GTx-007 showed lower potency and intrinsic activity in increasing the weights of prostate and seminal vesicle, but a greater potency and intrinsic activity in increasing the weight of levator ani muscle. Particularly, S-GTx-007, at a dose as low as 0.3 mg/day, was able to maintain the levator ani muscle weight of castrated animals in the same level as that of intact animals. Thus, S-GTx-007 is a potent nonsteroidal anabolic agent with less androgenic activity but more anabolic activity than testosterone propionate. This is a significant improvement over previous claims, in that this compound selectively stimulates muscle growth and other anabolic effects while having less effect on the prostate and seminal vesicles. This may be particularly relevant in aging men with concerns related to the development or progression of prostate cancer.

GTx-014 was less potent than GTx-007, but showed greater tissue selectivity (compare effects on the prostate and seminal vesicles in FIGS. 2 and 3). GTx-014 significantly increased levator ani muscle weights, but showed little to no ability to stimulate prostate and seminal vesicle growth (i.e., the prostate and seminal vesicle weights were less than 20% of that observed in intact animals or in animals treated with testosterone propionate).

Results showed that none of the examined compounds produced significant effect on body weight or the weights of other organs (i.e., liver, kidneys, spleen, lungs and heart). Nor did any compound produce any signs of acute toxicity, as gauged by diagnostic hematology tests and visual examination of animals receiving treatments. Importantly, GTx-007 did not suppress the production of luteinizing hormone (LH) or follicle stimulating hormone (FSH) at a dose of 0.3 mg/day (i.e., a dose that exhibited maximal anabolic effects).

In summary, S-GTx-007 exhibited exceptional anabolic activity in animals by maintaining the weight of levator ani muscle after removal of endogenous androgen. This discovery represents major progress towards the development of therapeutically useful nonsteroidal androgens, and a major improvement (i.e., tissue selectivity and potency) over previous drugs in this class. S-GTx-014 and S-GTx-007 showed selective anabolic activity in comparison with testosterone propionate, an androgenic and anabolic steroid. The tissue-selective activity is actually one of the advantages of nonsteroidal androgens in terms of anabolic-related applications.

Despite similarities in structure and in-vitro functional activity, the S-isomers of compounds GTx-014, GTx-015, GTx-016, and GTx-007 exhibited profound differences in terms of their in-vivo activity GTx-007 the most efficacious androgenic and anabolic activity in animals, with the anabolic activity greater than that of testosterone propionate. GTx-014 showed a small degree of androgenic activity, but an anabolic activity comparable to testosterone propionate. In contrast, GTx-015 and GTx-016 failed to produce any androgenic or anabolic activity in-vivo.

These studies show the discovery of two members (GTx-014 and GTx-007, compounds, compounds II and V respectively) of a new class of selective androgen receptor modulators (SARMS) that demonstrate potent anabolic effects (e.g., muscle growth) with less androgenic activity (e.g., prostatic growth). This new class of drugs has several advantages over nonselective androgens, including potential therapeutic applications in males and females for modulation of fertility, erythropoiesis, osteoporosis, sexual libido and in men with or at high risk for prostate cancer.

Figure 7:
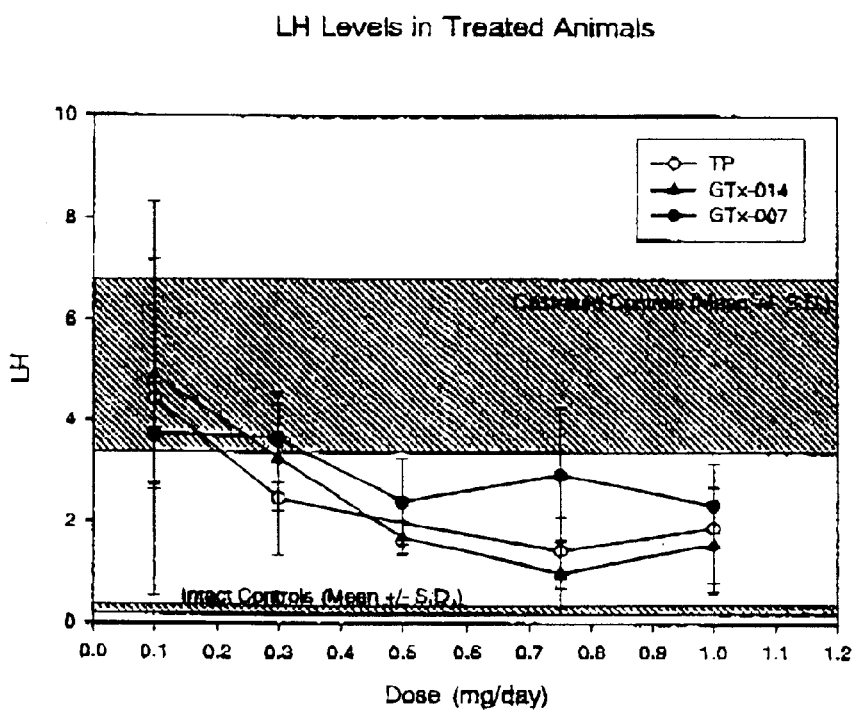
FIG. 7: Effects of GTx-014 and GTx-007 on LH Levels.
Figure 8:
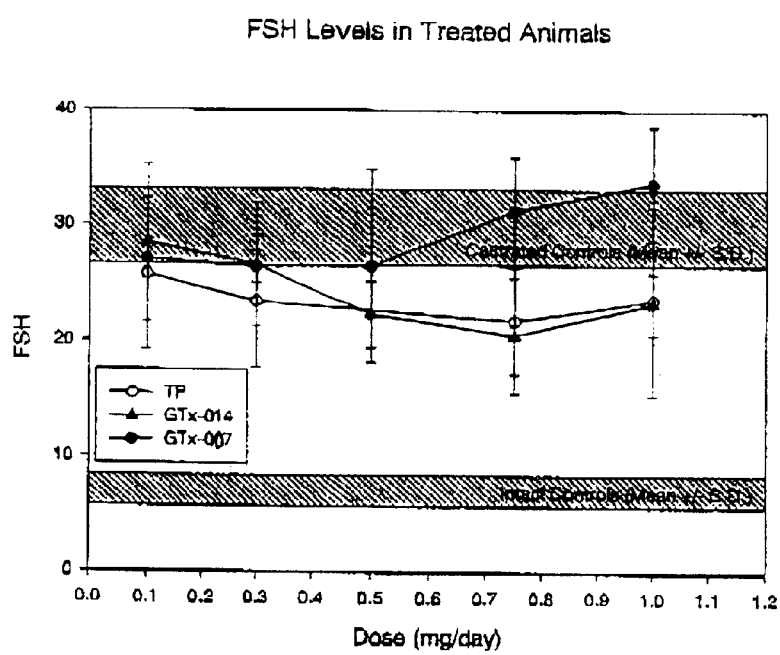
FIG. 8: Effects of GTx-014 and GTx-007 on FSH Levels.

Further, FIGS. 7 and 8 demonstrate the effects of GTx-014 and GTx-007 on LH and FSH levels in rats. These results further demonstrate the novelty of these SARM, due to their differential effects on these reproductive hormones, thus demonstrating the tissue-specific pharmacologic activity. In FIG. 7, LH levels in castrated animals treated with TP and GTx-014 were significantly lower than those of untreated animals (i.e., castrated controls) at doses greater than or equal to 0.3 mg/day. However, higher doses (i.e., 0.5 mg/day or higher) of GTx-007 were required before significant decreases in LH levels were observed. Thus, GTx-007 does not suppress LH levels at doses that are capable of eliciting maximal stimulation of levator ani muscle growth. In FIG. 8, FSH levels in castrated animals treated with GTx-014 were significantly lower than those of untreated animals (i.e., castrated controls) at doses of 0.5 mg/day or higher. Similarly, lower FSH levels were observed in animals treated with TP. However, only this difference was only significant at a dose of 0.75 mg/day. FSH levels in animals treated with GTx-007 were not significantly different from those of untreated animals at any dose level tested. Thus, GTx-007 does not suppress FSH levels at doses that are capable of eliciting maximal stimulation of levator ani muscle growth.

TABLE 1

Animals Groups and Experimental Design

| Group # | Castrated? | Drug | Dose | # of animals |
|---|---|---|---|---|
| 1 | No | None | None | 5 |
| 2 | Yes | None | Vehicle only | 5 |
| 3 | Yes | Testosterone | 0.1 mg/day | 5 |
| 4 | Yes | Testosterone | 0.3 mg/day | 5 |
| 5 | Yes | Testosterone | 0.5 mg/day | 5 |
| 6 | Yes | Testosterone | 0.75 mg/day | 5 |
| 7 | Yes | Testosterone | 1.0 mg/day | 5 |
| 8 | Yes | R-GTx-014 | 1.0 mg/day | 5 |
| 9 | Yes | S-GTx-014 | 0.1 mg/day | 5 |
| 10 | Yes | S-GTx-014 | 0.3 mg/day | 5 |
| 11 | Yes | S-GTx-014 | 0.5 mg/day | 5 |
| 12 | Yes | S-GTx-014 | 0.75 mg/day | 5 |
| 13 | Yes | S-GTx-014 | 1.0 mg/day | 5 |
| 14 | Yes | S-GTx-015 | 0.1 mg/day | 5 |
| 15 | Yes | S-GTx-015 | 0.3 mg/day | 5 |
| 16 | Yes | S-GTx-015 | 0.5 mg/day | 5 |
| 17 | Yes | S-GTx-015 | 0.75 mg/day | 5 |
| 18 | Yes | S-GTx-015 | 1.0 mg/day | 5 |
| 19 | Yes | S-GTx-016 | 0.1 mg/day | 5 |
| 20 | Yes | S-GTx-016 | 0.3 mg/day | 5 |
| 21 | Yes | S-GTx-016 | 0.5 mg/day | 5 |
| 22 | Yes | S-GTx-016 | 0.75 mg/day | 5 |
| 23 | Yes | S-GTx-016 | 1.0 mg/day | 5 |
| 24 | Yes | S-GTx-007 | 0.1 mg/day | 5 |
| 25 | Yes | S-GTx-007 | 0.3 mg/day | 5 |
| 26 | Yes | S-GTx-007 | 0.5 mg/day | 5 |
| 27 | Yes | S-GTx-007 | 0.75 mg/day | 5 |
| 28 | Yes | S-GTx-007 | 1.0 mg/day | 5 |
| 29 | Yes | None | Vehicle only | 5 |

EXAMPLE 3

Pharmacokinetics of GTx-007 in Dogs

Figure 4:
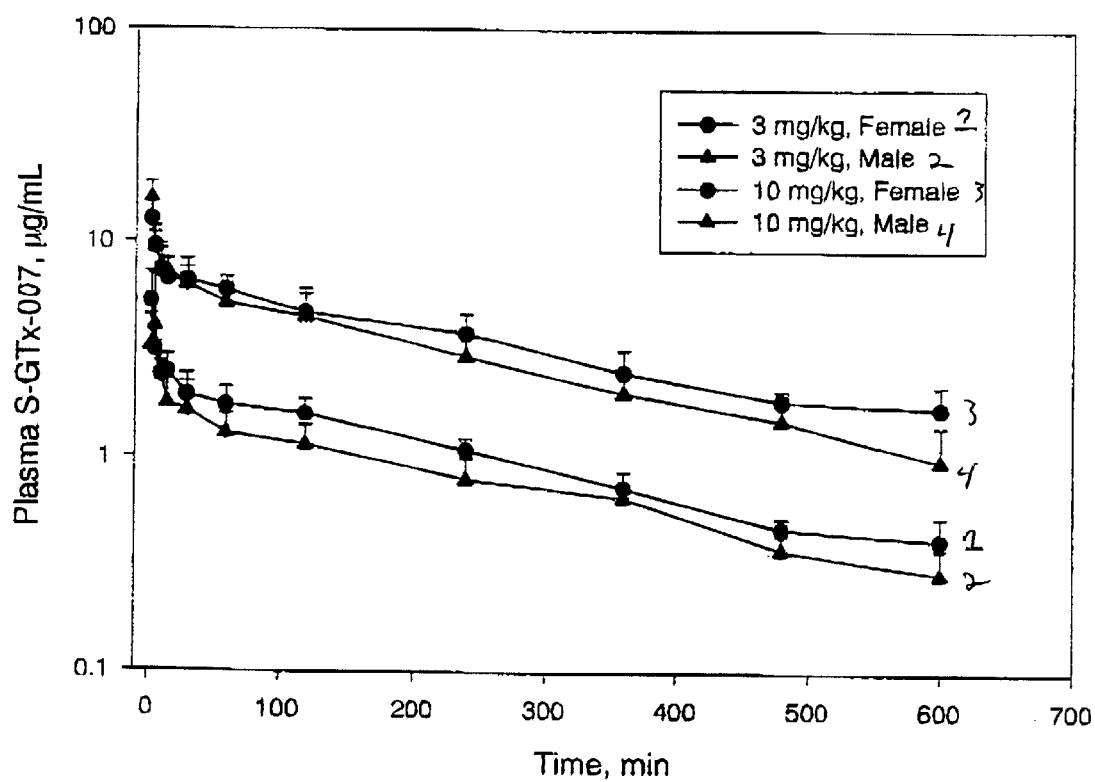
FIG. 4: Average plasma concentration-time profiles of S-GTx-007 in beagle dogs after IV administration at 3 and 10 mg/kg.
Figure 5:
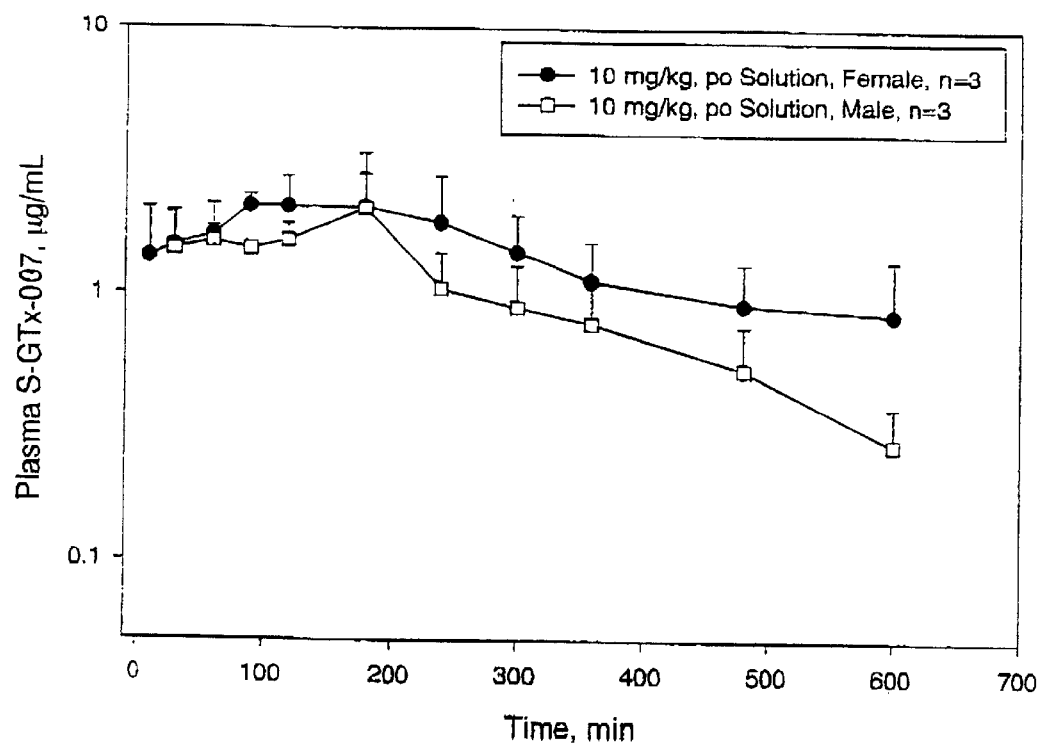
FIG. 5: Average plasma concentration-time profiles of S-GTx-007 in beagle dogs after PO administration as solution at 10 mg/kg.
Figure 6:
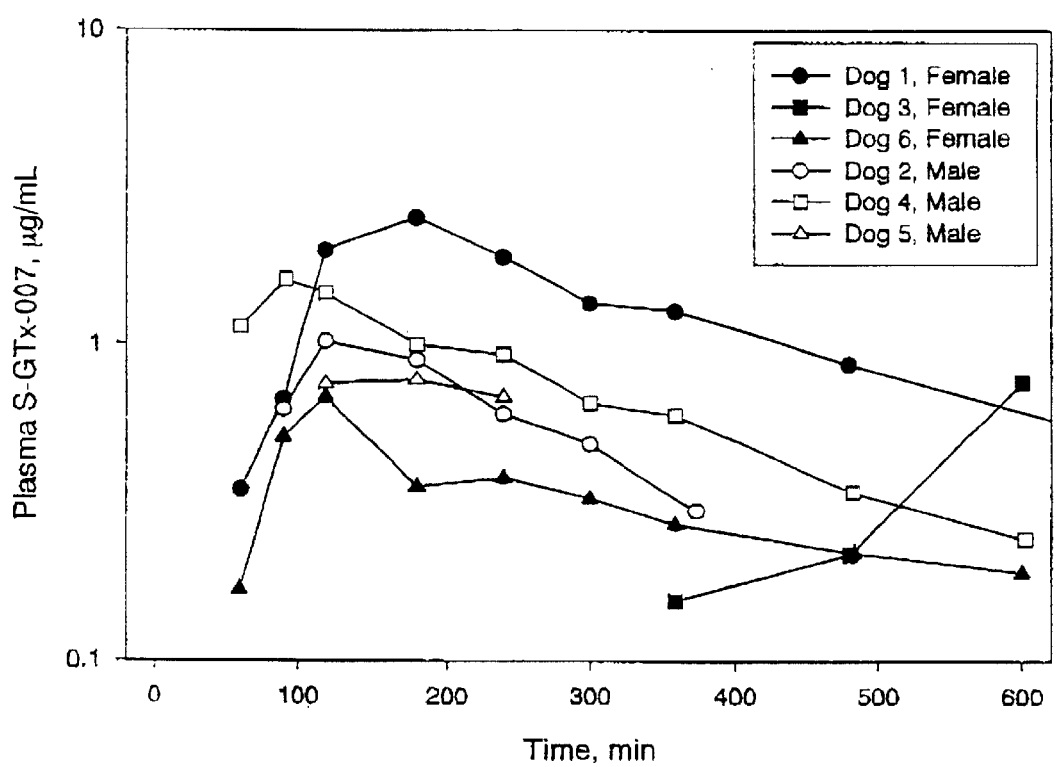
FIG. 6: Average plasma concentration-time profiles of S-GTx-007 in beagle dogs after IV administration as capsules at mg/kg.

The pharmacokinetics of S-GTx-007, a novel selective androgen receptor modulator (SARM), were characterized in beagle dogs. A four-treatment, four-period crossover design was utilized in the study, which involved a total of six beagle dogs, three of each gender. Each animal received a 3 mg/kg IV dose, a 10 mg/kg IV dose, a 10 mg/kg PO dose in solution, and a 10 mg/kg PO dose in capsule, in a randomly assigned order. There was an one-week washout period between treatments Plasma samples were collected for up to 72 hr after drug administration. Plasma S-GTx-007 concentrations were analyzed by a validated HPLC method. The clearance (CL), volume of distribution (Vss), half-life ($T_{1/2}$), and other pharmacokinetic parameters were determined by noncompartmental methods. Results showed that S-GTx-007 was cleared from dog plasma with a terminal $T_{1/2}$ of about 4 hr and a CL of 4.4 mL/min/kg after IV administration. FIGS. 4, 5, and 6 show the plasma concentration-time profiles of S-GTx-007 after administration of an intravenous solution, oral solution, and oral capsule, respectively. The Pharmacokinetics were dose- and gender-independent. The oral bioavailability of S-GTx-007 varied with the dosage form, and averaged 38% and 19% for solution and capsule, respectively. Thus, S-GTx-007 demonstrated moderate half-life, slow clearance and moderate bioavailability in beagle dogs, identifying it as the first of a new class of orally bioavailable tissue-selective androgen receptor modulators.

EXAMPLE 4

GTx-007 Analysis by HPLC

A reversed phase high pressure liquid chromatograph (HPLC) assay was developed to quantitate GTx-007 concentrations in dog plasma. Dog blood samples were obtained by venipuncture and centrifuged at 1000 g for 15 minutes. Samples were stored frozen at −20° C. until analysis. Individual samples were rapidly thawed and an aliquot (0.5 ml) was spiked with internal standard (20 μl of a 200 μg/ml aqueous solution of CM-II-87). An aliquot of 1 ml of acetonitrile was added to the samples to precipitate plasma proteins. The samples were vortexed and then centrifuged at 1000 g for 15 minutes. The supernatant was decanted into glass extraction tubes and 7.5 ml of ethyl acetate was added. The extraction mixture was left at room temperature for 20 minutes, and vortexed several times during this interval. The samples were then centrifuged at 1000 g for 10 minutes, and the organic phase was removed and placed in conical-bottomed glass tubes. The organic phase was evaporated under nitrogen. The samples were reconstituted in 200 μl of mobile phase (35:65 acetonitrile:water) and transferred to an autosampler vial for HPLC injection (Waters 717 plus autosampler, Waters Corp., Milford, Mass.). The isocratic mobile phase of 35% (v/v) acetonitrile in water was pumped at a flow rate of 1 ml/min (Model 510, Waters Corp.). The stationary phase was a C18 reversed phase column (Novapac C18, 3.9×150 mm). Analytes were monitored with UV detection at 270 nm (Model 486 absorbance detector, Waters Corp.). Retention times for GTx-007 and CM-II-87 were 11.1 and 16.9 minutes, respectively. Chromatography data was collected and analyzed using Millennium software. Plasma concentrations of GTx-007 in each sample were determined by comparison to calibration curves. Calibration curves were constructed by adding known amounts of GTx-007 to dog plasma. Final GTx-007 concentrations in dog plasma samples used in the calibration curves were 0.08, 0,2, 0.4, 2, 4, 10, and 20 μg/ml. Calibration curves were linear over this concentration range and exhibited correlation coefficients (r2) of 0.9935 or greater. Intra- and inter-day coefficients of variation for the standards ranged from 6.4% for 0.08 μg/ml to 7.9% for 20 μg/ml.

Melting points were determined on a Thomas-Hoover capillary melting point apparatus and are uncorrected. Infrared spectra were recorded on a Perkin Elmer System 2000 FT-IR. Optical rotations were determined on an Autopol® III Automatic Polarimeter (Rudolph Research Model III-589-10, Fairfield, N.J.). Proton and carbon-13 magnetic resonance spectra were obtained on a Bruker AX 300 spectrometer (300 and 75 MHz for $^1$H and $^{13}$C, respectively). Chemical shift values were reported as parts per million (δ) relative to tetramethylsilane (TMS). Spectral data were consistent with assigned structures. Mass spectra were determined on a Bruker-HP Esquire LC System. Elemental analyses were performed by Atlantic Microlab Inc. (Norcross, Ga.), and found values were within 0.4% of the theoretical values. Routine thin-layer chromatography (TLC) was performed on silica gel on aluminum plates (silica gel 60 F 254, 20×20 cm, Aldrich Chemical Company Inc., Milwaukee, Wis.). Flash chromatography was performed on silica gel (Merck, grade 60, 230–400 mesh, 60). Tetrahydrofuran (THF) was dried by distillation over sodium metal. Acetonitrile (MeCN) and methylene chloride ($CH_2Cl_2$) were dried by distillation from $P_2O_5$.

What is claimed is:

1. A composition comprising a selective androgen receptor modulator (SARM) compound having in-vivo androgenic and anabolic activity of a nonsteroidal ligand for the androgen receptor, said compound represented by the structure of formula (I):

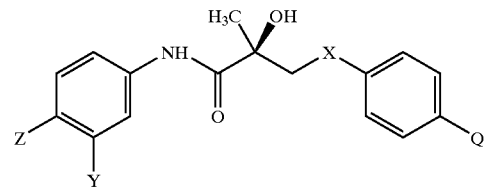

wherein
X is a O;
Z is $NO_2$, CN, COR, or CONHR;
Y is I, $CF_3$, Br, Cl, or $SnR_3$;
R is an alkyl group or OH; and
Q is acetamido or trifluroacetamido.

2. The composition according to claim 1, wherein Z is $NO_2$.

3. The composition according to claim 1, wherein Y is $CF_3$.

4. The composition according to claim 1, wherein Q is $NHCOCH_3$.

5. The composition according to claim 1, wherein Z is $NO_2$, Y is $CF_3$, and Q is $NHCOCH_3$.

6. A pharmaceutical composition comprising:
an effective amount of a selective androgen receptor modulator (SARM) compound having in-vivo androgenic and anabolic activity of a nonsteroidal ligand for the androgen receptor, said compound represented by the structure of formula (I):

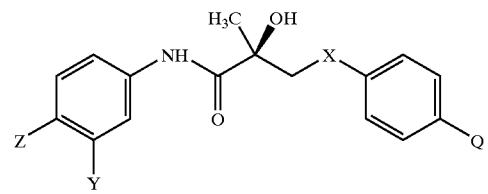

wherein
X is a O;
Z is $NO_2$, CN, COR, or CONHR;
Y is I, $CF_3$, Br, Cl, or $SnR_3$;
R is an alkyl group or OH;
Q is acetamido or trifluroacetamido; and
a pharmaceutically acceptable carrier, diluent or salt.

7. The pharmaceutical composition according to claim 6, wherein Z is $NO_2$.

8. The pharmaceutical composition according to claim 6, wherein Y is CF$_3$.

9. The pharmaceutical composition according to claim 6, wherein Q is NHCOCH$_3$.

10. The pharmaceutical composition according to claim 6, wherein Z is NO$_2$, Y is CF$_3$, and Q is NHCOCH$_3$.

11. A method of binding a selective androgen receptor modulator compound to an androgen receptor, comprising the step of contacting the androgen receptor with a selective androgen receptor modulator (SARM) compound having in-vivo androgenic and anabolic activity of a nonsteroidal ligand for the androgen receptor, in an amount effective to bind the selective androgen receptor modulator compound to the androgen receptor, wherein said compound is represented by the structure of formula (I):

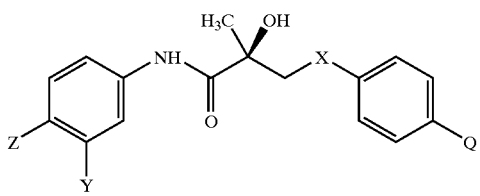

wherein
X is a O;
Z is NO$_2$, CN, COR, or CONHR;
Y is I, CF$_3$, Br, Cl, or SnR$_3$;
R is an alkyl group or OH; and
Q is acetamido or trifluroacetamido.

12. The method according to claim 11, wherein Z is NO$_2$.

13. The method according to claim 11, wherein Y is CF$_3$.

14. The method according to claim 11, wherein Q is NHCOCH$_3$.

15. The method according to claim 11, wherein Z is NO$_2$, Y is CF$_3$, and Q is NHCOCH$_3$.

16. A method of suppressing spermatogenesis in a subject, comprising the step of contacting an androgen receptor of the subject with a selective androgen receptor modulator (SARM) compound having in-vivo androgenic and anabolic activity of a nonsteroidal ligand for the androgen receptor, in an amount effective to suppress sperm production, wherein said compound is represented by the structure of formula (I):

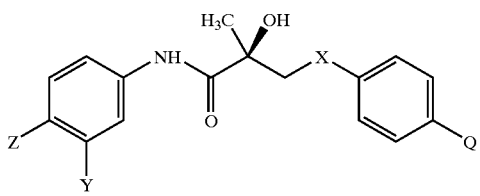

wherein
X is a O;
Z is NO$_2$, CN, COR, or CONHR;
Y is I, CF$_3$, Br, Cl, or SnR$_3$;
R is an alkyl group or OH; and
Q is acetamido or trifluroacetamido.

17. The method according to claim 16, wherein Z is NO$_2$.

18. The method according to claim 16, wherein Y is CF$_3$.

19. The method according to claim 16, wherein Q is NHCOCH$_3$.

20. The method according to claim 16, wherein Z is NO$_2$, Y is CF$_3$, and Q is NHCOCH$_3$.

21. A method of hormone therapy comprising the step of contacting an androgen receptor of a subject with a selective androgen receptor modulator (SARM) compound having in-vivo androgenic and anabolic activity of a nonsteroidal ligand for the androgen receptor, in an amount effective bind the selective androgen receptor modulator compound to the androgen receptor and effect a change in an androgen-dependent condition, wherein said compound is represented by the structure of formula (I):

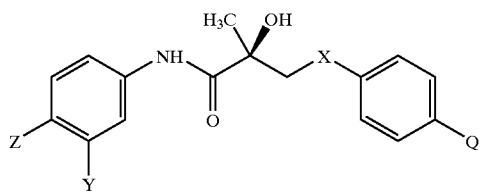

wherein
X is a O;
Z is NO$_2$, CN, COR, or CONHR;
Y is I, CF$_3$, Br, Cl, or SnR$_3$;
R is an alkyl group or OH; and
Q is acetamido or trifluroacetamido.

22. The method according to claim 21, wherein Z is NO$_2$.

23. The method according to claim 21, wherein Y is CF$_3$.

24. The method according to claim 21, wherein Q is NHCOCH$_3$.

25. The method according to claim 21, wherein Z is NO$_2$, Y is CF$_3$, and Q is NHCOCH$_3$.

26. A method of treating a subject having a related hormone condition, comprising the step of contacting an androgen receptor of the subject with a selective androgen receptor modulator (SARM) compound having in-vivo androgenic and anabolic activity of a nonsteroidal ligand for the androgen receptor, in an amount effective bind the selective androgen receptor modulator compound to the androgen receptor and effect a change in an androgen-dependent condition, wherein said compound is represented by the structure of formula (I):

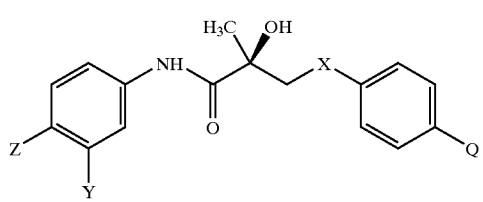

wherein
X is a O;
Z is NO$_2$, CN, COR, or CONHR;
Y is I, CF$_3$, Br, Cl, or SnR$_3$;
R is an alkyl group or OH; and
Q is acetamido or trifluroacetamido.

27. The method according to claim 26, wherein Z is NO$_2$.

28. The method according to claim 26, wherein Y is CF$_3$.

29. The method according to claim 26, wherein Q is NHCOCH$_3$.

30. The method according to claim 26, wherein Z is NO$_2$, Y is CF$_3$, and Q is NHCOCH$_3$.

* * * * *

UNITED STATES PATENT AND TRADEMARK OFFICE
CERTIFICATE OF CORRECTION

PATENT NO.    : 6,569,896 B2
DATED         : May 27, 2003
INVENTOR(S)   : Dalton, James T. et al.

It is certified that error appears in the above-identified patent and that said Letters Patent is hereby corrected as shown below:

<u>Title page,</u>
Item [63], Related U.S. Application Data, should read -- Continuation Application No. 09/644,970, filed on August 24, 2000, which was converted to Provisional Application Serial No. 60/367,355. --

Signed and Sealed this

Twenty-fourth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO.         : 6,569,896 B2                                     Page 1 of 1
APPLICATION NO. : 09/935045
DATED                : May 27, 2003
INVENTOR(S)        : James T. Dalton It is certified that error appears in the above-identified patent and that said Letters Patent is hereby corrected as shown below:

Column 24, line 62 – line should read --The pH of the mixture was kept at 10-11 during the addition of the metacryloly chloride.--

Signed and Sealed this

Twenty-eighth Day of August, 2007

JON W. DUDAS
*Director of the United States Patent and Trademark Office*